(12) United States Patent
Quincy, III et al.

(10) Patent No.: US 8,425,578 B2
(45) Date of Patent: Apr. 23, 2013

(54) WARMING PRODUCT

(75) Inventors: Roger B. Quincy, III, Cumming, GA (US); Susan Kathleen Cobbs, Atlanta, GA (US); Eugenio G. Varona, Marietta, GA (US); Jeffrey E. Fish, Dacula, GA (US); Clifford Jackson Ellis, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1762 days.

(21) Appl. No.: 11/513,830

(22) Filed: Aug. 31, 2006

(65) Prior Publication Data

US 2008/0082151 A1   Apr. 3, 2008

(51) Int. Cl.
   *A61F 7/00* (2006.01)
(52) U.S. Cl.
   USPC ... 607/96; 126/262; 126/263.01; 126/263.02; 126/263.05; 126/263.07
(58) Field of Classification Search .................. 126/262, 126/263.01, 263.02, 263.05, 263.07; 607/96
   See application file for complete search history.

(56) References Cited

U.S. PATENT DOCUMENTS

| | | | | |
|---|---|---|---|---|
| 2,144,811 | A | * | 1/1939 | Reynolds ................ 132/220 |
| 2,153,676 | A | * | 4/1939 | Reynolds ................ 132/220 |
| 2,573,791 | A | | 11/1951 | Howells |
| 2,935,983 | A | * | 5/1960 | Reik ................ 126/263.05 |
| 3,261,347 | A | | 7/1966 | Sherman |
| 3,976,049 | A | | 8/1976 | Yamashita et al. |
| 4,106,477 | A | | 8/1978 | Feld |
| 4,366,804 | A | | 1/1983 | Abe |
| 4,516,564 | A | | 5/1985 | Koiso et al. |
| 4,747,841 | A | | 5/1988 | Kuratomi et al. |
| 4,756,299 | A | | 7/1988 | Podella |
| 4,925,743 | A | | 5/1990 | Ikeda et al. |

(Continued)

FOREIGN PATENT DOCUMENTS

| | | |
|---|---|---|
| EP | 0370600 A1 | 7/1989 |
| EP | 0427475 A1 | 11/1990 |

(Continued)

OTHER PUBLICATIONS

Drobot, N.F., et al., *Inorganic Materials* vol. 40 No. 1 2004, p. 35.

(Continued)

*Primary Examiner* — Avinash Savani
(74) *Attorney, Agent, or Firm* — Dority & Manning, P.A.

(57) ABSTRACT

A warming product that contains an exothermic composition configured to generate heat in the presence of oxygen and moisture is provided. The exothermic composition is applied to a thermal composite containing two or more fibrous layers, which are structured to provide enhanced distribution of the exothermic composition through the thermal composite structure. For example, a first fibrous layer may rapidly acquire the exothermic composition and distribute it primarily in the −z direction (direction of thickness) to a second fibrous layer, which may then distribute the exothermic composition primarily in the −x and −y directions. Typically, at least a portion of the exothermic composition is able to flow through the second fibrous layer and contact additional layers. For example, the exothermic composition may contain a moisture-holding layer configured to supply moisture to the exothermic composition. This places the exothermic composition into close contact with the moisture-holding layer, which may provide enhanced heating efficiency. Further, the exothermic composition may also adhere the moisture-holding layer to the composite without the need for additional bonding mechanisms.

36 Claims, 5 Drawing Sheets

U.S. PATENT DOCUMENTS

| | | |
|---|---|---|
| 5,046,479 A | 9/1991 | Usui |
| 5,178,139 A | 1/1993 | Angelillo et al. |
| 5,366,491 A | 11/1994 | Ingram et al. |
| 5,398,667 A | 3/1995 | Witt |
| 5,407,741 A | 4/1995 | Ota |
| 5,425,975 A | 6/1995 | Koiso et al. |
| 5,454,363 A | 10/1995 | Sata |
| RE35,427 E | 1/1997 | Poettgen |
| 5,702,375 A | 12/1997 | Angelillo et al. |
| 5,770,528 A | 6/1998 | Mumick et al. |
| 5,879,378 A | 3/1999 | Usui |
| 5,918,590 A | 7/1999 | Burkett et al. |
| 5,925,072 A | 7/1999 | Cramer et al. |
| 5,975,074 A | 11/1999 | Koiso et al. |
| 5,984,995 A | 11/1999 | White |
| 6,019,782 A | 2/2000 | Davis et al. |
| 6,099,556 A | 8/2000 | Usui |
| 6,127,294 A | 10/2000 | Koiso et al. |
| 6,197,045 B1 | 3/2001 | Carson |
| 6,264,681 B1 | 7/2001 | Usui |
| 6,265,631 B1 | 7/2001 | Angelillo et al. |
| 6,436,128 B1 | 8/2002 | Usui |
| 6,648,909 B2 | 11/2003 | Helming |
| 6,770,064 B1 | 8/2004 | Ruscher |
| 6,791,004 B2 | 9/2004 | Sprengard-Eichel et al. |
| 6,863,682 B2 | 3/2005 | Usui |
| 7,081,211 B2 | 7/2006 | Li et al. |
| 2002/0045923 A1* | 4/2002 | Tone et al. ............ 607/96 |
| 2002/0121624 A1 | 9/2002 | Usui |
| 2002/0151947 A1* | 10/2002 | Usui ............ 607/111 |
| 2002/0161420 A1* | 10/2002 | Usui ............ 607/114 |
| 2004/0063603 A1 | 4/2004 | Dave et al. |
| 2004/0138598 A1 | 7/2004 | Kortuem et al. |
| 2004/0178384 A1 | 9/2004 | Usui |
| 2005/0028806 A1 | 2/2005 | Kumamoto et al. |
| 2006/0141882 A1 | 6/2006 | Quincy, III et al. |
| 2006/0142712 A1 | 6/2006 | Quincy, III |
| 2006/0142828 A1 | 6/2006 | Schorr et al. |
| 2006/0276863 A1 | 12/2006 | Kumamoto et al. |
| 2007/0020412 A1* | 1/2007 | Kumamoto et al. ......... 428/34.2 |
| 2007/0141929 A1 | 6/2007 | Quincy, III et al. |
| 2007/0142882 A1* | 6/2007 | Quincy et al. ............ 607/96 |
| 2007/0142883 A1 | 6/2007 | Quincy, III |
| 2007/0156213 A1 | 7/2007 | Friedensohn et al. |

FOREIGN PATENT DOCUMENTS

| | | |
|---|---|---|
| EP | 0786240 A1 | 7/1995 |
| EP | 0856302 A1 | 8/1998 |
| EP | 1112702 A1 | 7/1999 |
| EP | 1566156 A1 | 4/2004 |
| GB | 316878 | 6/1930 |
| GB | 2297430 A | 8/1996 |
| GB | 2312846 | 11/1997 |
| WO | WO 98/29079 | 7/1998 |
| WO | WO 99/09918 | 3/1999 |
| WO | WO 01/03619 A1 | 1/2001 |

OTHER PUBLICATIONS

Drobot, N.F., et al., *Inorganic Materials* vol. 38 No. 5 2002, p. 501.

Drobot, N.F., et al., *Inorganic Materials* vol. 38 No. 6 2002, p. 586.

Hoyland, et al., *Journal Paper Technology & Industry*, Dec. 1976, p. 291.

* cited by examiner

WARMING PRODUCT

BACKGROUND OF THE INVENTION

Certain metal powders (e.g., iron powder) are oxidized in the presence of air and moisture. Because the oxidation reaction is exothermic and generates heat, the metal powders have been incorporated into exothermic compositions to provide warmth. For example, conventional exothermic compositions contained a metal powder, activated carbon, and metal halide. The activated carbon acted as a catalyst to facilitate the exothermic reaction, while the metal halide removed surface oxide films on the metal powder to allow the reaction to proceed to a sufficient extent. Unfortunately, various problems existed when attempting to apply such exothermic compositions to a thermal composite. Specifically, if the exothermic composition were exposed to moisture during application, the exothermic reaction could occur prematurely. This ultimately would lower the quality of the exothermic composition and give rise to various other problems, such as an increased difficulty in handling due to coagulation. Various techniques were developed in an attempt to overcome these and other problems. For example, U.S. Pat. No. 6,436,128 to Usui describes an exothermic composition that contains an exothermic substance, a water-absorptive polymer and/or tackifier, a carbon component and/or metal halide, and water. An excessive amount of water is used in the composition to suppress a premature oxidation reaction with air. Once formulated, the exothermic composition of Usui is laminated and sealed in a thin pouch. The pouch absorbs water from the composition so that, when the seal is broken, the exothermic reaction may proceed upon exposure to air and moisture. Despite overcoming certain problems of conventional techniques, Usui is still too complex for many consumer applications. Moreover, it is often difficult to control the reaction rate of the exothermic substance in such devices.

As such, a need currently exists for an improved warming product that is simple, effective, and relatively inexpensive to make, and also readily controllable.

SUMMARY OF THE INVENTION

In accordance with one embodiment of the present invention, a warming product is disclosed that comprises a thermal composite. The thermal composite includes a first fibrous layer and a second fibrous layer, the permeability of the first fibrous layer being greater than the permeability of the second fibrous layer. The warming product further comprises an exothermic composition distributed through the first fibrous layer and the second fibrous layer of the composite, the exothermic composition comprising a metal configured to undergo an exothermic reaction upon exposure to oxygen and moisture.

In accordance with still another embodiment of the present invention, a method for forming a warming product is disclosed. The warming product contains a thermal composite that includes a first fibrous layer and a second fibrous layer. An exothermic coating formulation is formed that comprises a metal configured to undergo an exothermic reaction upon exposure to oxygen and moisture. An additional layer (e.g., moisture-holding layer) is positioned adjacent to the second fibrous layer of the thermal composite. The exothermic coating formulation is applied to one or more surfaces of the thermal composite so that at least a portion of the formulation flows through the first fibrous layer and the second fibrous layer and contacts the additional layer. The formulation adheres the additional layer to the composite.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF THE REPRESENTATIVE EMBODIMENTS

Definitions

Figure 1:
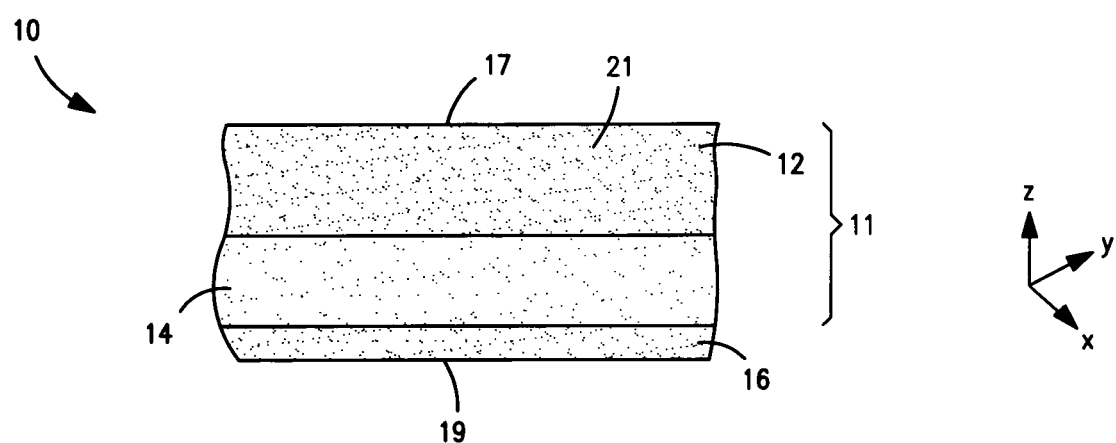
FIG. 1 illustrates a cross-sectional view of one embodiment of a warming product of the present invention.

As used herein the term "nonwoven" web or layer means a web having a structure of individual fibers or threads which are interlaid, but not in an identifiable manner as in a knitted fabric. Nonwoven webs may include, for instance, meltblown webs, spunbond webs, airlaid webs, carded webs, hydraulically entangled webs, etc. The basis weight of a nonwoven web may vary, such as from about 5 grams per square meter ("gsm") to 120 gsm, in some embodiments from about 10 gsm to about 70 gsm, and in some embodiments, from about 15 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Buntin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 micrometers, and are often between about 5 to about 20 micrometers.

As used herein, the term "coform" generally refers to a thermal composite material that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

Test Methods

Permeability:

The "du Plessis" Permeability may be calculated from the following equation:

$$\text{Permeability} = 0.051 * R * (1-\text{Porosity}) * (\text{Porosity}/[1-\text{Porosity}])^{2.75}$$

wherein,

R is the fiber radius; and

Porosity=(1−web density)/fiber density

Reference for the porosity equation may be found in the article "Quantification of Unidirectional Fiber Bed Permeability" by J. Westhuizen and J. P. du Plessis in the Journal of Composite Materials, 28(7), 1994, which is incorporated herein in its entirety by reference thereto for all purposes.

Permeability may also be calculated from the Kozeny-Carman equation, such as described in detail in U.S. Pat. No. 5,879,343 to Dodge II, et al.; U.S. Pat. No. 6,723,892 to Daley, et al.; an article by R. W. Hoyland and R. Field in the Journal Paper Technology and Industry, December 1976, p. 291-299 and Porous Media Fluid Transport and Pore Structure by F. A. L. Dullien, 1979, Academic Press, Inc. ISBN 0-12-223650-5, all of which are incorporated herein in their entirety by reference thereto for all purposes. The Kozeny-Carman equation is set forth below:

| Calculated Variable | | Equation | Dimensions |
|---|---|---|---|
| Permeability = | k | $= \dfrac{\varepsilon^3}{KS_0^2(1-\varepsilon)^2} \dfrac{1}{9.87 \times 10^{-9}}$ | Darcys |
| Kozeny Constant = | K | $= \dfrac{3.5\varepsilon^3}{(1-\varepsilon)^{0.5}}[1 + 57(1-\varepsilon)^3]$ | dimensionless |
| Surface area per mass of the material = | $S_V$ | $= \sum_i \dfrac{x_i}{r_{i,\mathit{eff}} \rho_i}$ | cm²/g |
| Mass weighted average component density = | $\rho_{avg}$ | $= \left(\sum_i \dfrac{x_i}{\rho_i}\right)^{-1}$ | g/cm³ |
| Surface area per solid volume of the material = | $S_0$ | $= S_V \rho_{avg}$ | cm⁻¹ |
| Porosity = | $\varepsilon$ | $= 1 - \sum_i x_i \dfrac{\rho_{web}}{\rho_i}$ | dimensionless |
| Effective fiber radius = | $r_{i,\mathit{eff}}$ | $= \dfrac{V_i}{SA_i}$ | cm |
| Density of web = | $\rho_{web}$ | $= \dfrac{BW}{10^3 \cdot t}$ | g/cm³ |
| for long cylinders | $r_{i,\mathit{eff}}$ | $= \dfrac{\frac{\pi d_i^2 L}{4}}{\pi d_i L} = \dfrac{d_i}{4 \times 10^4}$ | |
| for spheres | $r_{i,\mathit{eff}}$ | $= \dfrac{\frac{4}{3}\frac{\pi d_i^3}{8}}{\pi d_i^2} = \dfrac{d_i}{6 \times 10^4}$ | | where
$d_i$ = diameter of component i (microns)
$\rho_i$ = density of component i (g/cm³)
$x_i$ = mass fraction of component i in web
BW = weight of sample/area (g/m²)
t = thickness of sample (mm) under 0.05 psi (23.9 dyne/cm² or 2.39 Pascal (N/m²) load Permeability Example Calculation For a structure which contains 57% southern softwood pulp, 40% superabsorbent and 3% binder fiber, and has a basis weight of 617.58 g/m² and a bulk thickness of 5.97 mm at 0.05 psi the example permeability calculation follows.

The component properties are as follows (note shape is approximated):

| Component | Shape | Diameter $d_i$ (microns) | Density $\rho_i$ (g/cm³) | Mass Fraction $x_i$ |
|---|---|---|---|---|
| Southern softwood | Cylinder | 13.3 | 1.55 | 0.57 |
| Superabsorbent | Sphere | 1125 | 1.50 | 0.40 |
| Binder | Cylinder | 17.5 | 0.925 | 0.03 |

$$\rho_{web}(g/cm^3) = \frac{BW}{10^3 \cdot t}$$

$$\rho_{web}(g/cm^3) = \frac{617.58}{(5.97)10^3}$$

$$\rho_{web}(g/cm^3) = 0.1034$$

Caliper

The caliper (or bulk thickness) of a material is a measure of thickness and is measured at 0.05 psi with a Starret-type bulk tester, in units of millimeters.

Density:

The density is calculated by dividing the weight per unit area of a sample in grams per square meter (gsm) by the caliper of the sample in millimeters (mm) at 68.9 Pascals, and multiplying the result by 0.001 to convert the value to grams per cubic centimeter (g/cc). A total of three samples would be evaluated and averaged for the density values.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations.

Generally speaking, the present invention is directed to a warming product that contains an exothermic composition configured to generate heat in the presence of oxygen and moisture. The exothermic composition is applied to a thermal composite containing two or more fibrous layers, which are structured to provide enhanced distribution of the exothermic composition through the thermal composite structure. For example, a first fibrous layer may rapidly acquire the exothermic composition and distribute it primarily in the −z direction (direction of thickness) to a second fibrous layer, which may then distribute the exothermic composition primarily in the −x and −y directions. Typically, at least a portion of the exothermic composition is able to flow through the second fibrous layer and contact additional layers. For example, the exothermic composition may contain a moisture-holding layer configured to supply moisture to the exothermic composition. This places the exothermic composition into close contact with the moisture-holding layer, which may provide enhanced heating efficiency. Further, the exothermic composition may also adhere the moisture-holding layer to the composite without the need for additional bonding mechanisms.

The exothermic composition may be formed from a variety of different components, including oxidizable metals, carbon components, binders, electrolytic salts, and so forth. Examples of such metals include, but are not limited to, iron, zinc, aluminum, magnesium, and so forth. Although not required, the metal may be initially provided in powder form to facilitate handling and to reduce costs. Various methods for removing impurities from a crude metal (e.g. iron) to form a powder include, for example, wet processing techniques, such as solvent extraction, ion exchange, and electrolytic refining for separation of metallic elements; hydrogen gas ($H_2$) processing for removal of gaseous elements, such as oxygen and nitrogen; floating zone melting refining method. Using such techniques, the metal purity may be at least about 95%, in some embodiments at least about 97%, and in some embodiments, at least about 99%. The particle size of the metal powder may also be less than about 500 micrometers, in some embodiments less than about 100 micrometers, and in some embodiments, less than about 50 micrometers. The use of such small particles may enhance the contact surface of the metal with air, thereby improving the likelihood and efficiency of the desired exothermal reaction. The concentration of the metal powder employed may generally vary depending on the nature of the metal powder, and the desired extent of the exothermal/oxidation reaction. In most embodiments, the metal powder is present in the exothermic composition in an amount from about 40 wt. % to about 95 wt. %, in some embodiments from about 50 wt. % to about 90 wt. %, and in some embodiments, from about 60 wt. % to about 80 wt. %.

In addition to an oxidizable metal, a carbon component may also be utilized in the exothermic composition of the present invention. Without intending to be limited in theory, it is believed that such a carbon component promotes the oxidation reaction of the metal and acts as a catalyst for generating heat. The carbon component may be activated carbon, carbon black, graphite, and so forth. When utilized, activated carbon may be formed from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No. 5,834,114 to Economy, et al.; U.S. Pat. No. 6,517, 906 to Economy, et al.; U.S. Pat. No. 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes.

The exothermic composition may also employ a binder for enhancing the durability of the exothermic composition when applied to a thermal composite. As described in more detail below, the binder may also serve as an adhesive for bonding one thermal composite to another thermal composite. Generally speaking, any of a variety of binders may be used in the exothermic composition of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the latexes typically has a glass transition temperature of about 30° C. or less so that the flexibility of the resulting thermal composite is not substantially restricted. Moreover, the polymer also typically has a glass transition temperature of about −25° C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer latexes that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer latexes described above may be readily varied, as is well known in the art, by utilizing a stabilizing agent having the desired charge during preparation of the polymer latex. Specific carbon/polymer latex systems are described in more detail in U.S. Pat. Nos. 6,573,212; 6,639,004; 5,693,385; and 5,540,916. Activated carbon/polymer latex systems that may be used in the present invention include Nuchar® PMA, DPX-8433-68A, and DPX-8433-68B, all of which are available from MeadWestvaco Corp of Stamford, Conn.

If desired, the polymer latex may be crosslinked using any known technique in the art, such as by heating, ionization, etc. Preferably, the polymer latex is self-crosslinking in that external crosslinking agents (e.g., N-methylol acrylamide) are not required to induce crosslinking. Specifically, crosslinking agents may lead to the formation of bonds between the polymer latex and the thermal composite to which it is applied. Such bonding may sometimes interfere with the effectiveness of the thermal composite in generating heat. Thus, the polymer latex may be substantially free of crosslinking agents. Particularly suitable self-crosslinking polymer latexes are ethylene-vinyl acetate copolymers available from Celanese Corp. of Dallas, Tex. under the designation DUR-O-SET®) Elite (e.g., PE-25220A, PE-LV 25-432A). Alternatively, an inhibitor may simply be employed that reduces the extent of crosslinking, such as free radical scavengers, methyl hydroquinone, t-butylcatechol, pH control agents (e.g., potassium hydroxide), etc.

Although polymer latexes may be effectively used as binders in the present invention, such compounds sometimes result in a reduction in drapability and an increase in residual odor. Thus, the present inventors have discovered that water-soluble organic polymers may also be employed as binders, either alone or in conjunction with the polymer latexes, to alleviate such concerns. For example, one class of water-soluble organic polymers found to be suitable in the present invention is polysaccharides and derivatives thereof (e.g., cellulosic ethers). Polysaccharides are polymers containing repeated carbohydrate units, which may be cationic, anionic, nonionic, and/or amphoteric. In one particular embodiment, for instance, the polysaccharide is a nonionic, cationic, anionic, and/or amphoteric cellulosic ether. Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. No. 6,123,996 to Larsson, et al.; U.S. Pat. No. 6,248,880 to Karlson; and U.S. Pat. No. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the coating composition of the present invention are ethyl hydroxyethyl cellulose, methylethyl hydroxyethyl cellulose, methylethyl hydroxyethyl hydroxypropyl cellulose and methyl hydroxypropyl cellulose. In such embodiments, the hydroxyethyl groups typically constitute at least 30% of the total number of hydroxyalkyl groups, and the number of ethyl substituents typically constitutes at least 10% of the total number of alkyl substituents.

Particularly suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is methylcellulose having a degree of methoxyl substitution (DS) of 1.8. The degree of methoxyl substitution represents the average number of hydroxyl groups present on each anhydroglucose unit that have been reacted, which may vary between 0 and 3. One such cellulosic ether is METOLOSE SM-100, which is a methylcellulose commercially available from Shin-Etsu Chemical Co., Ltd. Other suitable cellulosic ethers are also available from Hercules, Inc. of Wilmington, Del. under the name "CULMINAL." Further examples of suitable polysaccharides are described in more detail above.

The concentration of the carbon component and/or binder in the exothermic composition may generally vary based on the desired properties of the thermal composite. For example, the amount of the carbon component is generally tailored to facilitate the oxidation/exothermic reaction without adversely affecting other properties of the thermal composite. Typically, the carbon component is present in the exothermic composition in an amount about 0.01 wt. % to about 20 wt. %, in some embodiments from about 0.1 wt. % to about 15 wt. %, and in some embodiments, from about 1 wt. % to about 12 wt. %. In addition, although relatively high binder concentrations may provide better physical properties for the exothermic composition, they may likewise have an adverse effect on other properties, such as the absorptive capacity of the thermal composite to which it is applied. Conversely, relatively low binder concentrations may reduce the ability of the exothermic composition to remain affixed on the thermal composite. Thus, in most embodiments, the binder is present in the exothermic composition in an amount from about 0.01 wt. % to about 20 wt. %, in some embodiments from about 0.1 wt. % to about 10 wt. %, and in some embodiments, from about 0.5 wt. % to about 8 wt. %.

Still other components may also be employed in the exothermic composition of the present invention. For example, as is well known in the art, an electrolytic salt may be employed to react with and remove any passivating oxide layer(s) that might otherwise prevent the metal from oxidizing. Suitable electrolytic salts may include, but are not limited to, alkali halides or sulfates, such as sodium chloride, potassium chloride, etc.; alkaline halides or sulfates, such as calcium chloride, magnesium chloride, etc., and so forth. When employed, the electrolytic salt is typically present in the exothermic composition in an amount from about 0.01 wt. % to about 10 wt. %, in some embodiments from about 0.1 wt. % to about 8 wt. %, and in some embodiments, from about 1 wt. % to about 6 wt. %.

In addition, particles may also be employed in the exothermic composition that act as moisture retainers. That is, prior to the oxidation/exothermic reaction, these particles may retain moisture. However, after the reaction has proceeded to a certain extent and the moisture concentration is reduced, the particles may release the moisture to allow the reaction to continue. Besides acting as a moisture retainer, the particles may also provide other benefits to the exothermic composition of the present invention. For example, the particles may alter the black color normally associated with the carbon component and/or metal powder. When utilized, the size of the moisture-retaining particles may be less than about 500 micrometers, in some embodiments less than about 100 micrometers, and in some embodiments, less than about 50 micrometers. Likewise, the particles may be porous. Without intending to be limited by theory, it is believed that porous particles may provide a passage for air and/or water vapors to better contact the metal powder. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, *Vol.* 60, 1938, p. 309, with nitrogen as the adsorption gas.

In one particular embodiment, porous carbonate particles (e.g., calcium carbonate) are used to retain moisture and also to alter the black color normally associated with activated carbon and/or metal powder. Such a color change may be more aesthetically pleasing to a user, particularly when the coating is employed on thermal composites designed for consumer/personal use. Suitable white calcium carbonate particles are commercially available in both dry and aqueous slurry form from Omya, Inc. of Proctor, Vt. Still other suitable inorganic particles that may retain moisture include, but are not limited to, silicates, such as calcium silicate, alumina silicates (e.g., mica powder, clay, etc.), magnesium silicates (e.g., talc), quartzite, calcium silicate fluorite, vermiculite, etc.; alumina; silica; and so forth. The concentration of the particles may generally vary depending on the nature of the particles, and the desired extent of exothermic reaction and color alteration. For instance, the particles may be present in the exothermic composition in an amount from about 0.01 wt. % to about 30 wt. %, in some embodiments from about 0.1 wt. % to about 20 wt. %, and in some embodiments, from about 1 wt. % to about 15 wt. %.

In addition to the above-mentioned components, other components, such as surfactants, pH adjusters, dyes/pigments/inks, viscosity modifiers, etc., may also be included in the exothermic coating of the present invention. Viscosity modifiers may be used, for example, to adjust the viscosity of the coating formulation based on the desired coating process and/or performance of the coated thermal composite. Suitable viscosity modifiers may include gums, such as xanthan gum. Binders, such as the cellulosic ethers, may also function as suitable viscosity modifiers. When employed, such additional components typically constitute less than about 5 wt. %, in some embodiments less than about 2 wt. %, and in some embodiments, from about 0.001 wt. % to about 1 wt. % of the exothermic coating.

To apply the exothermic composition to the thermal composite, the components may be initially dissolved or dispersed in a solvent. For example, one or more of the above-mentioned components of the exothermic composition may be mixed with a solvent, either sequentially or simultaneously, to form a coating formulation that may be easily applied to a thermal composite. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. The concentration of the solvent is generally high enough to inhibit oxidization of the metal prior to use. Specifically, when present in a high enough concentration, the solvent may act as a barrier to prevent air from prematurely contacting the oxidizable metal. If the amount of solvent is too small, however, the exothermic reaction may occur prematurely. Likewise, if the amount of solvent is too large, the amount of metal deposited on the thermal composite might be too low to provide the desired exothermal effect. Although the actual concentration of solvent (e.g., water) employed will generally depend on the type of oxidizable metal and the thermal composite on which it is applied, it is nonetheless typically present in an amount from about 10 wt. % to about 80 wt. %, in some embodiments from about 20 wt. % to about 70 wt. %, and in some embodiments, from about 25 wt. % to about 60 wt. % of the coating formulation.

The amount of the other components added to the coating formulation may vary depending on the amount of heat desired, the wet pick-up of the application method utilized, etc. For example, the amount of the oxidizable metal (in powder form) within the coating formulation generally ranges from about 20 wt. % to about 80 wt. %, in some embodiments from about 30 wt. % to about 70 wt. %, and in some embodiments, from about 35 wt. % to about 60 wt. %. In addition, the carbon component may constitute from about 0.1 wt. % to about 20 wt. %, in some embodiments from about 0.1 wt. % to about 15 wt. %, and in some embodiments, from about 0.2 wt. % to about 10 wt. %. of the coating formulation. Binders may constitute from about 0.01 wt. % to about 20 wt. %, in some embodiments from about 0.1 wt. % to about 15 wt. %, and in some embodiments, from about 1 wt. % to about 10 wt. % of the coating formulation. Electrolytic salts may constitute from about 0.01 wt. % to about 10 wt. %, in some embodiments from about 0.1 wt. % to about 8 wt. %, and in some embodiments, from about 1 wt. % to about 5 wt. %. of the coating formulation. Further, moisture-retaining particles (e.g., calcium carbonate) may constitute from about 2 wt. % to about 30 wt. %, in some embodiments from about 3 wt. % to about 25 wt. %, and in some embodiments, from about 4 wt. % to about 10 wt. %. of the coating formulation. Other components, such as surfactants, pH adjusters, viscosity modifiers, etc., may also constitute from about 0.001 wt. % to about 5 wt. %, in some embodiments from about 0.01 wt. % to about 1 wt. %, and in some embodiments from about 0.02 wt. % to about 0.5 wt. % of the coating formulation.

The solids content and/or viscosity of the coating formulation may be varied to achieve the desired amount of heat generation. For example, the coating formulation may have a solids content of from about 30% to about 80%, in some embodiments from about 40% to about 70%, and in some embodiments, from about 50% to about 60%. By varying the solids content of the coating formulation, the presence of the metal powder and other components in the exothermic composition may be controlled. For example, to form an exothermic composition with a higher level of metal powder, the coating formulation may be provided with a relatively high solids content so that a greater percentage of the metal powder is incorporated into the exothermic composition during the application process. In addition, the viscosity of the coating formulation may also vary depending on the coating method and/or type of binder employed. For instance, lower viscosities may be employed for saturation coating techniques (e.g., dip-coating), while higher viscosities may be employed for drop-coating techniques. Generally, the viscosity is less than about $2\times10^6$ centipoise, in some embodiments less than about $2\times10^5$ centipoise, in some embodiments less than about $2\times10^4$ centipoise, and in some embodiments, less than about $2\times10^3$ centipoise, such as measured with a Brookfield DV-1 viscometer with an LV spindle. If desired, thickeners or other viscosity modifiers may be employed in the coating formulation to increase or decrease viscosity.

The coating formulation may be applied using any conventional technique, such as bar, roll, knife, curtain, print (e.g., rotogravure), spray, slot-die, drop-coating, or dip-coating techniques. Regardless, the resulting composite is typically heated to a certain temperature to remove the solvent and any moisture from the coating. For example, the composite may be heated to a temperature of at least about 100° C., in some embodiments at least about 110° C., and in some embodiments, at least about 120° C. In this manner, the resulting dried exothermic composition is anhydrous, i.e., generally free of water. By minimizing the amount of moisture, the exothermic composition is less likely to react prematurely and generate heat. That is, the oxidizable metal does not generally react with oxygen unless some minimum amount of water is present. Thus, the exothermic composition may remain inactive until placed in the vicinity of moisture (e.g., next to a layer that contains moisture) during use. It should be understood, however, that relatively small amounts of water may still be present in the exothermic composition without causing a substantial exothermic reaction. In some embodiments, for example, the exothermic composition contains water in an amount less than about 0.5% by weight, in some embodiments less than about 0.1% by weight, and in some embodiments, less than about 0.01% by weight.

The solids add-on level of the exothermic composition may also be varied as desired. The "solids add-on level" is determined by subtracting the weight of the untreated thermal composite from the weight of the treated thermal composite (after drying), dividing this calculated weight by the weight of the untreated thermal composite, and then multiplying by 100%. Lower add-on levels may optimize certain properties (e.g., absorbency), while higher add-on levels may optimize heat generation. In some embodiments, for example, the add-on level is from about 100% to about 5000%, in some embodiments from about 200% to about 2400%, and in some embodiments, from about 400% to about 1200%. The thickness of the exothermic composition may also vary. For example, the thickness may range from about 0.01 millimeters to about 5 millimeters, in some embodiments, from about 0.01 millimeters to about 3 millimeters, and in some embodiments, from about 0.1 millimeters to about 2 millimeters. In some cases, a relatively thin coating may be employed (e.g., from about 0.01 millimeters to about 0.5 millimeters). Such a thin coating may enhance the flexibility of the thermal composite, while still providing uniform heating.

The coating formulation may cover an entire surface of the thermal composite, or may only cover a portion of the surface. For instance, to maintain absorbency, porosity, flexibility, and/or some other characteristic of the thermal composite, it may sometimes be desired to apply the exothermic composition so as to cover less than 100%, in some embodiments from about 10% to about 80%, and in some embodiments, from about 20% to about 60% of the area of one or more surfaces of the thermal composite. In one particular embodiment, the exothermic composition is applied to the thermal composite in a preselected pattern (e.g., reticular pattern, diamond-shaped grid, dots, and so forth). It should be understood, however, that the coating may also be applied uniformly to one or more surfaces of the thermal composite. In addition, a patterned exothermic composition may also provide different functionality to each zone. For example, in one embodiment, the thermal composite is treated with two or more patterns of coated regions that may or may not overlap. The regions may be on the same or different surfaces of the thermal composite. In one embodiment, one region of a thermal composite is coated with a first exothermic composition, while another region is coated with a second exothermic composition. If desired, one region may provide a different amount of heat than another region.

Besides having functional benefits, the thermal composite may also have various aesthetic benefits as well. For example, although containing activated carbon, the thermal composite may be made without the black color commonly associated with activated carbon. In one embodiment, white or light-colored particles (e.g., calcium carbonate, titanium dioxide, etc.) are employed in the exothermic composition so that the resulting thermal composite has a grayish or bluish color. In addition, various pigments, dyes, and/or inks may be employed to alter the color of the exothermic composition. The thermal composite may also be applied with patterned regions of the exothermic composition to form a thermal composite having differently colored regions.

Generally speaking, the exothermic coating formulation may be applied to one or more surfaces of the thermal composite. In most embodiments, the coating formulation is applied so that at least a portion of the formulation flows through a first fibrous layer of the composite into a second fibrous layer. The formulation may then optionally contact an additional layer (e.g., moisture-holding layer) positioned adjacent to the second fibrous layer of the composite. In this manner, for example, the exothermic formulation may be positioned close to the source of moisture for the exothermic reaction and may also serve to adhere the composite to the moisture-holding layer.

Referring to FIG. 1, for example, one embodiment of a warming product 10 that may be formed in accordance with the present invention is shown. As shown, the warming product 10 defines two outer surfaces 17 and 19, and is in the form of a substantially flat, conformable, and foldable material. The overall size and shape of the warming product 10 are not critical. For example, the warming product 10 may have a shape that is generally triangular, square, rectangular, pentagonal, hexagonal, circular, elliptical, etc. Likewise, the warming product 10 may have a relatively small total thickness. For example, the warming product 10 may have a total thickness of from about 0.1 to about 100 millimeters, in some embodiments from about 0.5 to about 80 millimeters, and in some embodiments, from about 1 to about 50 millimeters.

Regardless, the warming product 10 contains a thermal composite 11 formed from a first fibrous layer 12 and a second fibrous layer 14. Any type of fibrous layers may generally be employed in the present invention, such as nonwoven webs, woven fabrics, knit fabrics, paper web, etc. When utilized, the nonwoven webs may include, but are not limited to, spunbonded webs (apertured or non-apertured), meltblown webs, carded webs (bonded or unbonded), airlaid webs, coform webs, hydraulically entangled webs, and so forth. A wide variety of polymers may be used, such as polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; and so forth.

Monocomponent and/or multicomponent fibers may be used to form the layers 12 and 14. Monocomponent fibers are generally formed from a polymer extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Multicomponent fibers may, for instance, be desirable to help provide mechanical integrity and stabilization to the thermal composite. Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The nonwoven web is optionally bonded using known techniques.

Although not necessarily required, the fibrous layer 12 and 14 are typically bonded together to form the composite structure. Any conventional bonding technique may be employed, such as through-air bonding, ultrasonic bonding, thermal point bonding, adhesive bonding, etc. For instance, the layers 12 and 14 may be thermally bonded together at a plurality of discrete sites by passing the layers through two or more rolls, one or both of which are heated to melt-fuse the fibers. One or both of the rolls may also contain intermittently raised bond points to provide an intermittent bonding pattern. The pattern of the raised points is generally selected so that the composite has a total bond area of less than about 50% (as determined by conventional optical microscopic methods), and in some embodiments, less than about 30%. Likewise, the bond density is also typically greater than about 100 bonds per square inch, and in some embodiments, from about 250 to about 500 pin bonds per square inch. Such a combination of total bond area and bond density may be achieved by bonding the web with a pin bond pattern having more than about 100 pin bonds per square inch that provides a total bond surface area less than about 30% when fully contacting a smooth anvil roll. In some embodiments, the bond pattern may have a pin bond density from about 250 to about 350 pin bonds per square inch and a total bond surface area from about 10% to about 25% when contacting a smooth anvil roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown, which are incorporated herein in their entirety by reference thereto for all purposes.

Regardless of the particular manner in which the layers are constructed, the permeability (relates to the volume of voids or spaces per gram of fibers) of the first fibrous layer 12 is greater than that of the second fibrous layer 14 such that a permeability gradient is formed. In this manner, an exothermic composition 21 may initially enter the first fibrous layer 12 at a fast rate due to its large void sizes, but then be slowed by the small void sizes of the second fibrous layer 14 so that it does penetrate completely therethrough.

The permeability of the fibrous layers 12 and 14 may be expressed in terms of the Kozeny-Carman and/or du Plessis permeability, such as described above. For instance, the second fibrous layer 14 may have a Kozeny-Carman permeability of from about 300 to about 4000 Darcies, and in some embodiments, from about 500 to about 3000 Darcies, and a du Plessis permeability of from about 500 to about 6000 Darcies, and in some embodiments, from about 650 to about 4500 Darcies. Likewise, the first fibrous layer 12 may have a Kozeny-Carman permeability of from about 1,500 to about 20,000 Darcies, and in some embodiments, from about 3,000 to about 17,500 Darcies, and a du Plessis permeability of from about 2,500 to about 35,000 Darcies, and in some embodiments, from about 4,000 to about 30,000 Darcies. Although the actual permeability values may vary somewhat depending on the test method employed, the relative difference in permeabilities between the layers is substantially the same. That is, the first fibrous layer 12 has a permeability greater than the second fibrous layer 14. For example, the ratio of the permeability of the first fibrous layer 12 to the permeability of the second fibrous layer 14 may be about 1.5 or more, in some embodiments about 2.0 or more, and in some embodiments, from about 2.5 to about 8.0.

The basis weight and caliper (or bulk thickness) of the second fibrous layer 14 may be the same or different than the first fibrous layer 12. In some embodiments, the basis weight of the second fibrous layer 14 may be less than the first fibrous layer 12. For example, the second fibrous layer 14 may have a basis weight of from about 1 to about 100 gsm, in some embodiments, from about 5 to about 75 gsm, and in some embodiments, from about 10 to about 50 gsm. The first fibrous layer 12, on the other hand, may have a basis weight of from about 25 to about 500 grams per square meter ("gsm"), in some embodiments from about 50 to about 300 gsm, and in some embodiments, from about 75 to about 250 gsm. Similarly, the caliper of the second fibrous layer 14 may also be less than the first fibrous layer 12. For example the caliper of the second fibrous layer 14 may range from about 0.01 to about 1 millimeter ("mm"), in some embodiments from about 0.05 to about 0.75 mm, and in some embodiments, from about 0.1 to about 0.5 mm. The caliper of the first fibrous layer 12, on the other hand, may range from about 0.75 to about 10 mm, in some embodiments from about 1 to about 5 mm, and in some embodiments, from about 1.5 to about 4 mm.

The manner in which the permeability gradient across the layers 12 and 14 is created may generally vary. For example, the first and second fibrous layers 12 and 14 may be formed from substantially similar fibers. In such embodiments, the second fibrous layer 14 may be further densified to establish a permeability gradient through compaction or addition of other components, such as absorbent gelling material, superabsorbent polymers, silica, foam, thermobondable fibers, charcoal, zeolites, etc. Alternatively, the permeability gradient may be established by varying the fiber type, size, and so forth.

In one particular embodiment, the denier (i.e., coarseness or fineness) of the fibers may be varied to achieve the desired permeability gradient. Coarser fibers (i.e., those having higher deniers) are more resilient and less structurally compressive and thus allow for the creation of greater void volumes. In contrast, finer fibers (i.e., those having lower deniers) are less resilient and more structurally compressive and thus allow for the creation of greater compaction and fewer void volumes. In this regard, the first fibrous layer 12 may contain fibers of a higher denier than those of the second fibrous layer 14. Typically, the average denier of the fibers in the first fibrous layer 12 is greater than the average denier of the fibers in the second fibrous layer 14 such that the ratio of the average deniers is about 1.1 or more, in some embodiments about 1.5 or more, and in some embodiments, from about 2.0 to about 10.0. For example, the average denier of the fibers in the first fibrous layer 12 may range from about 3 to about 30, in some embodiments from about 5 to about 25, and in some embodiments, from about 8 to about 20. Likewise, the average denier of the fibers in the second fibrous layer 14 may range from about 0.1 to about 10, in some embodiments from about 0.5 to about 8, and in some embodiments, from about 1 to about 6.

Mixtures of small denier fibers and large denier fibers may also be used to further enhance liquid wicking and distribution properties. Namely, the use of differently sized fibers may result in the formation of voids of varying sizes and in multiple planes, which enhances intake and wicking of the exothermic composition 21. In one particular embodiment, for example, the first fibrous layer 12 contains a mixture of small and large denier fibers in which the small denier fibers have a denier of at least 2, in some embodiments at least 3, and in some embodiments, at least 5 less than the large denier fibers. For instance, the small denier fibers may have a denier of from about 2 to about 10, while the large denier fibers may have a denier of from about 4 to about 20. The relative percentage of the fibers may also vary. For example, the small denier fibers may constitute from about 25 wt. % to about 75 wt. %, and in some embodiments, from about 40 wt. % to about 60 wt. % of the fiber mixture. Likewise, the large denier fibers may constitute from about 25 wt. % to about 75 wt. %, and in some embodiments, from about 40 wt. % to about 60 wt. % of the fiber mixture. Although the second fibrous layer 14 may also contain a mixture of small and large denier fibers, it preferably contains fibers of approximately the same size so that they tend to form similarly sized pores in a single plane, thereby enhancing the −z directional barrier properties of the layer.

In one particular embodiment, the first fibrous layer 12 is a nonwoven web that contains a mixture of polyester staple fibers and polyethylene-polypropylene (sheath-core) bicomponent fibers. The second fibrous layer 14 may be a nonwoven web that contains polyethylene-polypropylene (sheath-core) bicomponent fibers. For instance, the first fibrous layer 12 may be a bonded carded web and the second fibrous layer may be a bonded or unbonded carded web. Various examples of such carded materials are described in U.S. Pat. No. 5,667,625 to Alikhan; U.S. Pat. No. 5,817,394 to Alikhan, et al.; and U.S. Pat. No. 6,781,027 to Fenwick, et al., which are incorporated herein in their entirety by reference thereto for all purposes.

The fibers of the layers 12 and 14 may be hydrophobic in nature and thus not readily receptive of the exothermic composition. However, the fibers may optionally be rendered hydrophilic through any known treatment for enhancing wettability. In one embodiment, for example, fibers of one or both layers may be applied with a treatment composition that contains a water-soluble organic polymer (e.g., polysaccharides and derivatives thereof) such as described above. The treatment composition may also employ surfactants to enhance the hydrophilic nature of the fibers. Ionic surfactants (i.e., anionic, cationic, or amphoteric surfactants) and/or nonionic surfactants may be employed in the treatment composition. Particularly suitable surfactants are nonionic surfactants, such as alkyl glycosides, ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

In one particular embodiment, alkyl glycosides are employed as a surface treatment for the fibers. Alkyl glycosides are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543, which are incorporated herein in their entirety by reference thereto for all purposes, describe alkyl glycosides and/or methods for their preparation. Commercially available examples of suitable alkyl glycosides include Glucopon™ 220, 225, 425, 600 and 625, all of which are available from Cognis Corp. of Cincinnati, Ohio. These products are mixtures of alkyl mono- and oligoglucopyranosides with alkyl groups based on fatty alcohols derived from coconut and/or palm kernel oil. Glucopon™ 220, 225 and 425 are examples of particularly suitable alkyl polyglycosides. Glucopon™ 220 is an alkyl polyglycoside that contains an average of 1.4 glucosyl residues per molecule and a mixture of 8 and 10 carbon alkyl groups (average carbons per alkyl chain-9.1). Glucopon™ 225 is a related alkyl polyglycoside with linear alkyl groups having 8 or 10 carbon atoms (average alkyl chain-9.1 carbon atoms) in the alkyl chain. Glucopon™ 425 includes a mixture of alkyl polyglycosides that individually include an alkyl group with 8, 10, 12, 14 or 16 carbon atoms (average alkyl chain-10.3 carbon atoms). Glucopon™ 600 includes a mixture of alkyl polyglycosides that individually include an alkyl group with 12, 14 or 16 carbon atoms (average alkyl chain 12.8 carbon atoms). Glucopon™ 625 includes a mixture of alkyl polyglycosides that individually include an alkyl group having 12, 14 or 18 carbon atoms (average alkyl chain 12.8 carbon atoms). Still other suitable alkyl glycosides are available from Dow Chemical Co. of Midland, Mich. under the Triton™ designation, e.g., Triton™ CG-110 and BG-10.

The fibers may be applied with the treatment composition using any known application technique. Desirably, the fibers are treated before being incorporated into a web or combined with other fibers into a web. Suggested methods of treatment include, but are not limited to, saturation, spray, slot die, printing, foaming, and combinations and modifications thereof. In a saturation process, tows of fiber bundles are dipped in a bath containing the treating solution. Fibers are impregnated with treating solution and excess solution can optionally be removed by nipping between nip rolls. Alternatively, the treating solution is sprayed onto a tow of fibers followed by drying. The tows of fibers can be treated one time or several times in consecutive steps if desired. Also a combination of processes can also be used such as for example a saturation step followed by a spray of same or different chemical. Various other application techniques and treatment compositions are described in U.S. Patent Application Publication Nos. 2002/0069988 to Yahiaoui, et al. and 2005/0136773 to Yahiaoui, et al., which are incorporated herein in their entirety by reference thereto for all purposes.

Referring again to FIG. 1, the exothermic composition 21 may be applied to the surface 17 of the warming product 10, which in this embodiment, is defined by the first fibrous layer 12. Consequently, the composition 21 may flow through the first fibrous layer 12 and into the second fibrous layer 14. Although the comparative low permeability of the second fibrous layer 14 forces a majority of the composition 21 in the −x and −y directions of the structure, at least a portion of the composition 21 flows through the layer 14 and contacts a moisture-holding layer 16 positioned adjacent thereto. In this manner, one or more components of the exothermic composition (e.g., binder) may function as an adhesive for attaching the moisture-holding layer 16 to the thermal composite 11. This also allows the application of the exothermic composition to occur concurrently with formation of the warming product 10, thereby enhancing processing efficiency and facilitating the ease in which the exothermic composition is applied.

The moisture-holding layer 16 helps control the moisture application rate by holding moisture and controllably releasing it to the exothermic composition over an extended period of time. Thus, moisture may be supplied directly from the moisture-holding layer 16 to the exothermic composition contained within the thermal composite 11. The moisture-holding layer 16 may contain an absorbent web formed using any technique, such as a dry-forming technique, an airlaying technique, a carding technique, a meltblown or spunbond technique, a wet-forming technique, a foam-forming technique, etc. Airlaid webs, for instance, are made from bundles of fibers having typical lengths ranging from about 3 to about 19 millimeters, which are separated, entrained in an air supply, and then deposited onto a forming surface, usually with the assistance of a vacuum supply. The randomly deposited fibers then are bonded to one another using, for example, hot air or an adhesive.

The moisture-holding layer 16 typically contains cellulosic fibers, such as natural and/or synthetic fluff pulp fibers. The fluff pulp fibers may be kraft pulp, sulfite pulp, thermomechanical pulp, etc. In addition, the fluff pulp fibers may include high-average fiber length pulp, low-average fiber length pulp, or mixtures of the same. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and so forth. Northern softwood kraft pulp fibers may be used in the present invention. One example of commercially available southern softwood kraft pulp fibers suitable for use in the present invention include those available from Weyerhaeuser Company with offices in Federal Way, Wash. under the trade designation of "NB-416." Another type of fluff pulp that may be used in the present invention is identified with the trade designation CR1654, available from U.S. Alliance of Childersburg, Ala., and is a bleached, highly absorbent sulfate wood pulp containing primarily softwood fibers. Still another suitable fluff pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

If desired, the moisture-holding layer 16 may also contain synthetic fibers, such as monocomponent and multicomponent (e.g., bicomponent) fibers. The moisture-holding layer

16 may also include a superabsorbent material, such as natural, synthetic and modified natural materials. Superabsorbent materials are water-swellable materials capable of absorbing at least about 20 times its weight and, in some cases, at least about 30 times its weight in an aqueous solution containing 0.9 weight percent sodium chloride. Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Other suitable absorbent gelling materials are disclosed in U.S. Pat. No. 3,901,236 to Assarsson et al.; U.S. Pat. No. 4,076,663 to Masuda et al.; and U.S. Pat. No. 4,286,082 to Tsubakimoto et al., which are incorporated herein in their entirety by reference thereto for all purposes.

When utilized, the superabsorbent material may constitute from about 1 wt. % to about 40 wt. %, in some embodiments, from about 5 wt. % to about 30 wt. %, and in some embodiments, from about 10 wt. % to about 25 wt. % of the moisture-holding layer 16 (on a dry basis). Likewise, synthetic fibers may constitute from about 1 wt. % to about 30 wt. %, in some embodiments, from about 2 wt. % to about 20 wt. %, and in some embodiments, from about 5 wt. % to about 15 wt. % of the moisture-holding layer 16 (on a dry basis). The cellulosic fibers may also constitute up to 100 wt. %, in some embodiments from about 50 wt. % to about 95 wt. %, and in some embodiments, from about 65 wt. % to about 85 wt. % of the moisture-holding layer 16 (on a dry basis).

The evaporation rate of moisture from the moisture-holding layer 16 may be controlled to achieve the desired heating profile. By controlling the evaporation rate, the desired amount of moisture may be released to the exothermic composition within a given period of time. For example, it is normally desired that the average "evaporation rate" of moisture from the moisture-holding layer 16 is from about 0.05% to about 0.5%, in some embodiments from about 0.10% to about 0.25%, and in some embodiments, from about 0.15% to about 0.20% per minute. The "evaporation rate" is determined by measuring the weight of moisture-holding layer 16 at a certain time, subtracting this measured weight from the initial wet weight of the layer, dividing this value by the initial wet weight, and then multiplying by 100. The evaporation rates are calculated for several different times and then averaged. The evaporation rate is determined in the present invention at a relative humidity of 51% and temperature of about 22° C. It should be understood that these relative humidity and temperature conditions are "initial" conditions in that they may vary during testing due to the increased presence of water vapor in the atmosphere.

In some embodiments, the desired evaporation rate of moisture is achieved by controlling the nature of the aqueous solution applied to the moisture-holding layer 16. Namely, the present inventors have discovered that the application of only water (vapor pressure of 23.7 mm Hg at 25° C.) to the moisture-holding layer 16 may sometimes result in too great of an evaporation rate. Thus, a solute may be added to the aqueous solution to reduce its vapor pressure, i.e., the tendency of the water molecules to evaporate. At 25° C., for example, the solute may be added so that the aqueous solution added to the moisture-holding layer 16 has an evaporation rate of less than 23.7 mm Hg, in some embodiments less than about 23.2 mm Hg, and in some embodiments, from about 20.0 mm Hg to about 23.0 mm Hg. One particularly suitable class of solutes includes organic and/or inorganic metal salts. The metal salts may contain monovalent (e.g., $Na^+$), divalent (e.g., $Ca^{2+}$), and/or polyvalent cations. Examples of preferred metal cations include the cations of sodium, potassium, calcium, aluminum, iron, magnesium, zirconium, zinc, and so forth. Examples of preferred anions include halides, chlorohydrates, sulfates, citrates, nitrates, acetates, and so forth. Particular examples of suitable metal salts include sodium chloride, sodium bromide, potassium chloride, potassium bromide, calcium chloride, etc. The actual concentration of the solute in the aqueous solution may vary depending on the nature of the solute, the particular configuration of the warming product, and the desired heating profile. For example, the solute may be present in the aqueous solution in an amount from about 0.1 wt. % to about 25 wt. %, in some embodiments from about 1 wt. % to about 20 wt. %, and in some embodiments, from about 5 wt. % to about 15 wt. % of the solution.

In addition to controlling aspects of the aqueous solution, the moisture-holding layer 16 itself may be selectively tailored to achieve the desired evaporation rate. For example, moisture-holding layers having a relatively low density and basis weight tend to release too great an amount of moisture in comparison to those having a higher density and basis weight. Without intending to be limited by theory, it is believed that such high density and high basis weight webs may have a lower porosity, thereby making it more difficult for moisture to escape from the layer over an extended period of time. Thus, in one embodiment of the present invention, the moisture-holding layer 16 (e.g., airlaid web) may have a density of from about 0.01 to about 0.50, in some embodiments from about 0.05 to about 0.25, and in some embodiments, from about 0.05 to about 0.15 grams per cubic centimeters ($g/cm^3$). In addition, the basis weight of the moisture-holding layer 16 may be from about 50 to about 500 grams per square meter ("gsm"), in some embodiments from about 100 to about 300 gsm, and in some embodiments, from about 150 to about 300 gsm.

Other techniques may also be employed to achieve the desired evaporation rate of moisture from the moisture-holding layer 16. For example, superabsorbent materials are capable of swelling in the presence of an aqueous solution. Swelling increases the absorption capacity of the moisture-holding layer 16, but likewise reduces the evaporation rate of moisture as the materials exhibit a greater tendency to "hold onto" the water molecules. Thus, the evaporation rate may be increased by reducing the degree of swelling. One technique for reducing the degree of swelling of a superabsorbent material involves reducing the temperature of the aqueous solution to below ambient temperature, such as less than about 25° C., and in some embodiments, from about 5° C. to about 20° C. The degree of swelling of the superabsorbent material may also be reduced by incorporating one or more ionic compounds into the aqueous solution to increase its ionic strength. The ionic compounds may be the same as the solutes described above. The "ionic strength" of a solution may be determined according to the following equation:

$$I = 0.5 * \Sigma_i z_i^2 * m_i$$

wherein, $z_i$ the valence factor; and $m_i$ is the concentration. For example, the ionic strength of a solution containing 1 molar calcium chloride and 2 molar sodium chloride is "3" and determined as follows:

$$I=0.5*[(2^2*1)+(1^2*2)]=3$$

Without intending to be limited by theory, it is believed that superabsorbent materials have a counterion atmosphere surrounding the ionic backbone of the polymer chains that collapses when its ionic strength is increased. Specifically, the counterion atmosphere is made up of ions of opposite charge to the charges along the backbone of a superabsorbent polymer and are present in the ionic compound (e.g., sodium or potassium cations surrounding the carboxylate anions distributed along the backbone of a polyacrylate anionic polymer). As the concentration of ions contacting the superabsorbent polymer increases, the ion concentration gradient in the liquid phase from the exterior to the interior of the polymer begins to decrease and the counterion atmosphere thickness ("Debye thickness") may be reduced from about 20 nanometers (in pure water) to about 1 nanometer or less. When the counterion atmosphere is highly extended, the counterions are more osmotically active and therefore promote a higher degree of liquid absorbency. To the contrary, when the ion concentration in the absorbed liquid increases, the counterion atmosphere collapses and the absorption capacity is diminished. As a result of the reduction in absorption capacity, the superabsorbent material exhibits less of a tendency to hold the water molecules, thereby allowing its release to the exothermic composition.

Although various configurations of a warming product have been described above, it should be understood that other configurations are also included within the scope of the present invention. For instance, other layers may also be employed to improve the exothermic properties of the warming product. For example, a first thermal composite may be employed in conjunction with a second thermal composite. The thermal composites may function together to provide heat to a surface, or may each provide heat to different surfaces. In addition, thermal composites may be employed that are not applied with the exothermic composition of the present invention, but instead applied with a coating that simply facilitates the reactivity of the exothermic composition. For example, a thermal composite may be used near or adjacent to the thermal composite of the present invention that includes a coating of moisture-retaining particles. As described above, the moisture-retaining particles may retain and release moisture for activating the exothermic reaction.

Still other layers may also be employed in the warming product if desired. For example, the warming product may contain a thermally conductive layer to help distribute heat toward the direction of a user (i.e., −z direction) and/or along the x-y plane of the device, thereby improving the uniformity of heat application over a selected area. The thermally conductive layer may have a coefficient of thermal conductivity of at least about 0.1 Watts per meter-Kelvin (W/m-K), and in some embodiments, from about 0.1 to about 10 W/m-k.

Although any conductive material may generally be employed, it is often desired that the selected material be conformable to enhance the comfort and flexibility of the warming product. Suitable conformable materials include, for instance, fibrous materials (e.g., nonwoven webs), films, and so forth. Optionally, the conductive layer may be vapor-permeable so that air may contact the thermal composite when desired to activate the exothermic reaction. One type of vapor-permeable, conformable material that may be used in the conductive layer is a nonwoven web material. For example, the conductive layer may contain a nonwoven laminate, such as a spunbonded/meltblown/spunbonded ("SMS") laminate. Such SMS laminates may also provide liquid strike-through protection and breathability. The SMS laminate is formed by well-known methods, such as described in U.S. Pat. No. 5,213,881 to Timmons, et al., which is incorporated herein its entirety by reference thereto for all purposes. Another type of vapor-permeable, conformable material that may be used in the conductive layer is a breathable film. For example, the conductive layer may sometimes utilize a breathable film/nonwoven laminate.

Regardless of the materials selected, a variety of techniques may be employed to provide conductivity to the conductive layer. For example, in some embodiments, a metallic coating may be utilized to provide conductivity. Metals suitable for such a purpose include, but are not limited to, copper, silver, nickel, zinc, tin, palladium, lead, copper, aluminum, molybdenum, titanium, iron, and so forth. Metallic coatings may be formed on a material using any of a variety of known techniques, such as vacuum evaporation, electrolytic plating, etc. For instance, U.S. Pat. No. 5,656,355 to Cohen; U.S. Pat. No. 5,599,585 to Cohen; U.S. Pat. No. 5,562,994 to Abba, et al.; and U.S. Pat. No. 5,316,837 to Cohen, which are incorporated herein their entirety by reference thereto for all purposes, describes suitable techniques for depositing a metal coating onto a material. Besides a metal coating, still other techniques may be employed to provide conductivity. For example, in one embodiment, an additive may be incorporated into the material (e.g., fibers, film, etc.) to enhance conductivity. Examples of such additives include, but are not limited to, carbon fillers, such as carbon fibers and powders; metallic fillers, such as copper powder, steel, aluminum powder, and aluminum flakes; and ceramic fillers, such as boron nitride, aluminum nitride, and aluminum oxide. Commercially available examples of suitable conductive materials include, for instance, thermally conductive compounds available from LNP Engineering Plastics, Inc. of Exton, Pa. under the name Konduit® or from Cool Polymers of Warwick, R.I. under the name CoolPoly®. Although several examples of conductive materials have been described above, it should be understood that any known conductive material may be generally used in the present invention.

In addition to a conductive layer, still other optional layers may be employed to enhance the effectiveness of the warming product. For example, an insulation layer may be employed to inhibit heat dissipation to the outer environment so that heat is instead focused toward the patient or user. Because the insulation layer increases the overall heat-producing efficiency of the device, the desired temperature increase may be reached with a lower amount of exothermic coating or other reactant (i.e., moisture or oxygen). The insulation layer may have a coefficient of thermal conductivity of less than about 0.1 Watts per meter-Kelvin (W/m-K), and in some embodiments, from about 0.01 to about 0.05 W/m-k.

Generally speaking, any known insulation material may be employed in the present invention. If desired, the selected insulation material may be fibrous in nature to improve the overall conformability of the warming product. The fibrous material may possess high loft to enhance its insulative properties. Suitable high loft materials may include porous woven materials, porous nonwoven materials, etc. Particularly suitable high loft materials are nonwoven multicomponent (e.g., bicomponent) polymeric webs. For example, the multicomponent polymers of such webs may be mechanically or chemically crimped to increase loft. Examples of suitable high loft materials are described in more detail in U.S. Pat.

No. 5,382,400 to Pike, et al.; U.S. Pat. No. 5,418,945 to Pike, et al.; and U.S. Pat. No. 5,906,879 to Huntoon, et al., which are incorporated herein in their entirety by reference thereto for all purposes. Still other suitable materials for use as an insulation material are described in U.S. Pat. No. 6,197,045 to Carson, which is incorporated herein in its entirety by reference thereto for all purposes.

The warming product may also include layers that optionally form outer surfaces. These layers may present a compliant, soft feeling, and non-irritating surface to the user's skin. For example, the layers may be formed from materials that are liquid- and vapor-permeable, liquid-impermeable and vapor-permeable ("breathable"), and so forth. Breathable layers may also be employed that permits the flow of water vapor and air for activating the exothermic reaction, but prevents an excessive amount of liquids from contacting the exothermic composition, which could either suppress the reaction or result in an excessive amount of heat that overly warms or burns the user. Various breathable layers are described, for instance, in U.S. Patent Application Publication No. 2006/0142828 to Schorr, et al., which is incorporated herein in its entirety by reference thereto for all purposes. It should be understood that numerous other possible combinations and configurations would be well within the ordinary skill of those in the art.

Regardless of the particular construction employed, a heating profile may be achieved for the warming product in which an elevated temperature is reached quickly and maintained over an extended period of time. For example, an elevated temperature of from about 30° C. to about 60° C., in some embodiments from about 35° C. to about 55° C., and in some embodiments from about 37° C. to about 43° C., may be achieved in 20 minutes or less, and in some embodiments, 10 minutes or less. This elevated temperature may be substantially maintained for at least about 1 hour, in some embodiments at least about 2 hours, in some embodiments at least about 4 hours, and in some embodiments, at least about 10 hours (e.g., for overnight use).

Moisture may be applied any time prior to or during use of the warming product, such as just prior to use or during manufacture. For example, water may be pre-applied to the moisture-holding layer as described above. The moisture is added in an amount effective to activate an exothermic, electrochemical reaction between the electrochemically oxidizable element (e.g., metal powder) and the electrochemically reducible element (e.g., oxygen). Although this amount may vary depending on the reaction conditions and the amount of heat desired, the moisture is typically added in an amount from about 20 wt. % to about 500 wt. %, and in some embodiments, from about 50 wt. % to about 200 wt. %, of the weight of the amount of oxidizable metal present in the coating. Although not necessarily required, it may be desired to seal such water-treated warming products within a substantially liquid-impermeable material and vapor-impermeable that inhibits the exothermic composition from contacting enough oxygen to prematurely activate the exothermic reaction. To generate heat, the warming product is simply removed from the package and exposed to air.

The warming product of the present invention may be employed in a wide range of articles to provide a warming effect. For example, the warming product may be used as a heating pad, bandage, food warmer, animal warmer, water warmer, and so forth. The warming product may also be used to deliver warmth in various other applications, such as drapes or blankets for warming patients during surgical or medical procedures.

The present invention may be better understood with reference to the following examples.

EXAMPLE 1

Initially, a 7"-wide roll of a single layer bonded carded web fabric was provided that had a basis weight of 1.5 ounces per square yard (50 grams per square meter). The fabric was formed from a blend of 60 wt. % bicomponent fibers and 40 wt. % polyester fibers. The bicomponent fibers were obtained from FiberVisions, Inc. of Covington, Ga. under the name "ESC 215", which had a polyethylene sheath and polypropylene core, a denier of 1.5 (23.6 μm), and 0.55 wt. % "HR6" finish. The polyester fibers were obtained from Invista of Wichita, Kan. under the name "T-295", which had a denier of 6.0 (29.3 μm) and contained a 0.5 wt. % L1 finish.

The coating formulation was prepared as follows. In a 1-gallon metal pail, 45.8 grams of METOLOSE SM-100 (Shin-Etsu Chemical Co., Ltd.) and 115.5 grams of sodium chloride (Mallinckrodt) were added to 1555.0 grams of distilled water that was stirred and heated to 73° C. The mixture was stirred and allowed to cool as the following additional ingredients were added sequentially: 180.9 grams of DUR-O-SET® Elite PE 25-220A ethylene-vinyl acetate emulsion (Celanese Emulsions), 433.0 grams of XP-5200-6 sample #05.2435503 calcium carbonate slurry (Omya), 95.5 grams of Nuchar SA-400 activated carbon (MeadWestvaco), and 1566.0 grams of A-131 iron powder (North American Höganäs). After about 100 minutes of stirring the formulation with all ingredients, the temperature was reduced with an ice bath to about 17° C. A noticeable increase in viscosity occurred when the temperature was reduced. The calculated concentration of each component of the aqueous formulation is set forth below in Table 1.

TABLE 1

| Components of the Aqueous Formulation | |
|---|---|
| Component | Calculated Amount |
| Iron | 39.2% |
| Activated Carbon | 2.4% |
| SM-100 | 1.2% |
| Elite PE | 2.2% |
| Calcium Carbonate | 3.7% |
| Sodium Chloride | 2.9% |
| Water | 48.4% |

The aqueous formulation was applied to one side of the 1.5 osy bonded carded web fabric using a knife coater. An airlaid fabric was used as a bottom layer to carry the coated bonded carded web fabric. The airlaid was formed from 75 wt. % wood pulp fluff (Weyerhaeuser NB416), 15 wt. % superabsorbent (Degussa SXM9543), and 10 wt. % of KoSa T255 bicomponent fiber, and had a basis weight of 225 grams per square meter and a density of 0.12 grams per cubic centimeter. The gap between the knife and steel roller that carried the bonded carded web and airlaid fabrics was set at 1540 micrometers. The line speed was 0.25 meters per minute. The coater contained a four-foot drier set at 145° C. that was used to partially dry the coated fabric. The partially dried coated fabric was attached to the bottom airlaid layer due to the aqueous formulation penetrating through the bonded carded web and contacting the airlaid. The partially dried coated laminate was cut into 17-inch pieces and placed in a laboratory oven at 110° C. for about 20 minutes to complete the drying step. The concentration of the components of the exothermic composition was calculated from the coated and dried laminate pieces (43.8±2.5 grams), the untreated pieces of bonded carded web and airlaid fabrics (15.6 grams), and the composition of the aqueous formulation. The results are set forth below in Table 2.

TABLE 2

Components of the Exothermic Composition

| Component | Calculated Amount |
|---|---|
| Iron | 76.1% |
| Activated Carbon | 4.6% |
| SM-100 | 2.2% |
| Elite PE | 4.3% |
| Sodium Chloride | 5.6% |
| Calcium Carbonate | 7.2% |
| Solids Add-On Level | ~180% |

A two-layered structure (3.5"×4") was then designed for activating the exothermic reaction. Specifically, the two-layered structure included two pieces of the coated bonded carded web airlaid laminate positioned with the airlaid side of each piece facing each other. The airlaid side of each piece of the laminate was first wetted with 3.4 and 3.5 grams of an aqueous salt solution, an amount that increased the mass of the airlaid layer of the laminate by a factor of about 2.7. The salt solution contained 10.0 wt. % sodium chloride in distilled water. The total weight of the two coated laminate pieces was 15.8 grams (8.1 grams of iron). The two-layered structure was then placed inside of a rectangular pouch (4.5"×4.8") that was sealed with a heat sealer. The pouch was made from a nylon spunbond microporous film laminate that had a layer of stapleknit fabric heat sealed to the nylon spunbond side. The laminate was obtained from Mitsubishi International Corp. and labeled TSF EDFH 5035-TYPE. The WVTR of the laminate was measured at 455 g/m$^2$/24 hrs by using the cup method (ASTM Standard E-96E-80). The stapleknit fabric was produced from 20% wood pulp fluff (50% Northern softwood kraft fibers/50% Alabama Pine bleached kraft softwood), 58% 1.5 denier polyester fiber (Invista Type 103), and 22% polypropylene spunbond (Kimberly-Clark Corp.). The resulting thermal device was heat sealed in a metallized storage bag for 1 day prior to activating the reaction. The metallized storage bag was KAL-ML5 from Kapak Corporation, a two-ply structure containing a metallized polyester layer that was adhesively laminated to a linear low density polyethylene film.

EXAMPLE 2

A thermal device was formed as described in Example 1, except that a 0.75 osy spunbond/meltblown/spunbond (SMS) fabric was used as a carrier sheet to keep the aqueous formulation from contacting the process components. The gap between the knife and steel roller that carried the bonded carded web and SMS fabrics was set at 1100 micrometers. The line speed was 0.25 meters per minute. When the coated fabric was removed from the SMS carrier sheet, the aqueous formulation had penetrated and wetted out the underside of the 1.5 osy bonded carded web fabric. The concentration of the components of the exothermic composition was calculated from the coated and dried fabric pieces (42.3±1.6 grams), the untreated piece of fabric (3.6 grams), and the composition of the aqueous formulation. The results are set forth below in Table 3.

TABLE 3

Components of the Exothermic Composition

| Component | Calculated Amount |
|---|---|
| Iron | 76.1% |
| Activated Carbon | 4.6% |
| SM-100 | 2.2% |
| Elite PE | 4.3% |
| Sodium Chloride | 5.6% |
| Calcium Carbonate | 7.2% |
| Solids Add-On Level | ~1069% |

A five-layered structure (3.5"×4") was then designed for activating the exothermic reaction. Specifically, the five-layered structure included one of the coated fabric pieces positioned on one side of a moisture-holding layer, and another coated fabric piece positioned on the other side of the moisture-holding layer. The uncoated side of the fabric pieces faced the moisture-holding layer. The moisture-holding layer was formed from 75 wt. % wood pulp fluff (Weyerhaeuser NB416), 15 wt. % superabsorbent (Degussa SXM9543), and 10 wt. % of KoSa T255 bicomponent fiber, and had a basis weight of 225 grams per square meter and a density of 0.12 grams per cubic centimeter. A "separation layer" was used to separate the moisture-holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture-holding layer (2.2 grams) was wetted on each side by spraying 6.3 grams of an aqueous salt solution, an amount that increased the mass of the layer by a factor of 3.9. The salt solution contained 10.0 wt. % sodium chloride in distilled water. Then the separation layer was placed around it with the fabric side of the separation layer in contact with the wetted moisture-holding layer. A coated layer was then placed on each side with the uncoated side in contact with the film side of the separation layer. The total weight of the two coated layers was 11.6 grams (8.0 grams of iron). The five-layered structure was then placed inside of a rectangular pouch (4.5"× 4.8") that was sealed with a heat sealer. The pouch was made from a nylon spunbond microporous film laminate that had a layer of stapleknit fabric heat sealed to the nylon spunbond side. The laminate was obtained from Mitsubishi International Corp. and labeled TSF EDFH 5035-TYPE. The WVTR of the laminate was measured at 455 g/m$^2$/24 hrs by using the cup method (ASTM Standard E-96E-80). The stapleknit fabric was produced from 20% wood pulp fluff (50% Northern softwood kraft fibers/50% Alabama Pine bleached kraft softwood), 58% 1.5 denier polyester fiber (Invista Type 103), and 22% polypropylene spunbond (Kimberly-Clark Corp.). The resulting thermal device was heat sealed in a metallized storage bag for 1 day prior to activating the reaction. The metallized storage bag was KAL-ML5 from Kapak Corporation, a two-ply structure containing a metallized polyester layer that was adhesively laminated to a linear low density polyethylene film.

EXAMPLE 3

Figure 2:
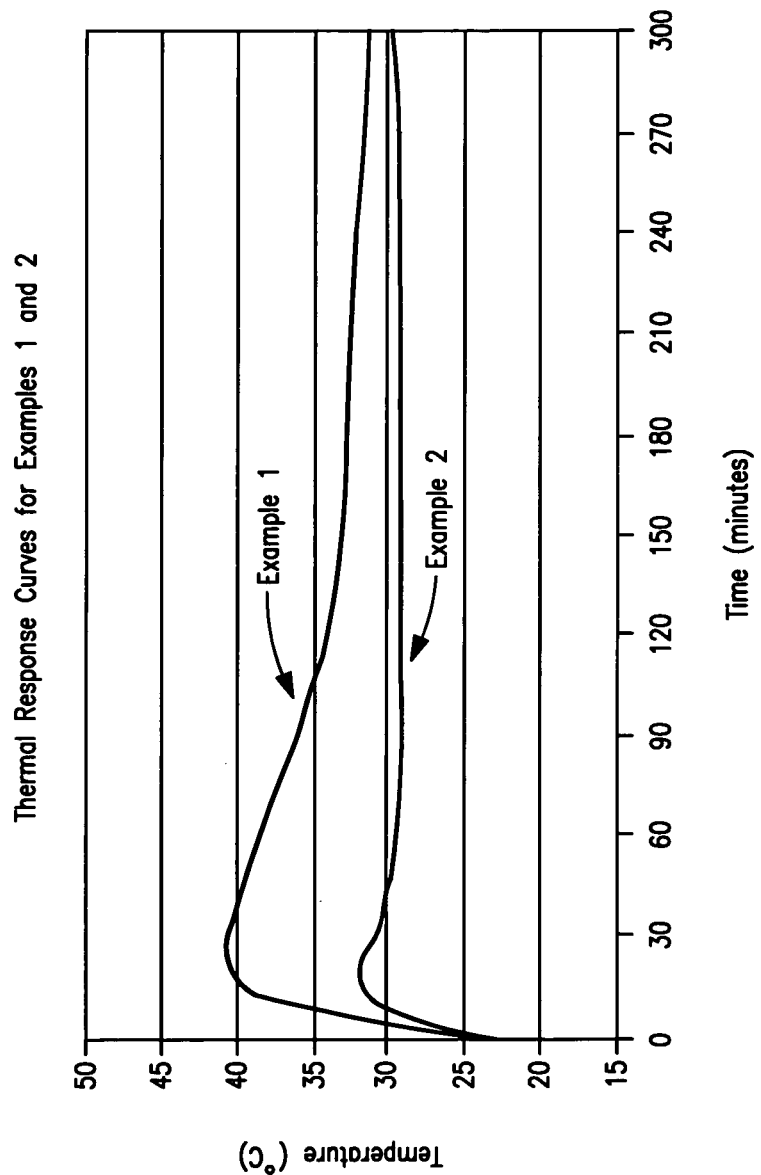
FIG. 2 is a thermal response curve showing temperature (° C.) versus time (minutes) for Examples 1 and 2.

The thermal devices of Examples 1 and 2 were tested for their thermal responsiveness by opening the metallized storage bags to initiate the reaction. Testing was conducted by attaching a thermocouple wired to a data collection device to one side of the thermal device. The temperature was recorded as a function of time (at 5 second intervals) to give the thermal response curves shown in FIG. 2. As illustrated, the thermal response curve for the device of Example 1 (contained the exothermic moisture holding fabric laminate) reached 40° C. within about 10 minutes after opening the storage bag, and also remained at a higher temperature over a 5-hour time period relative to the device of Example 2.

EXAMPLE 4

Initially, a 7"-wide roll of a dual layer bonded carded composite was provided. The first layer contained 58 gsm of a blend of 40% 6.0 denier (28.5 μm) Invista T-295 polyester fiber with 0.50% L1 finish and 60% of a 28 denier (59.3 μm) FiberVisions ESC bicomponent (PE sheath/PP core) fiber with 0.55% HR6 finish. The second layer contained 17 gsm of a 100% 1.5 denier (20.4 μm) FiberVisions ESC 215 bicomponent (PE sheath/PP core) fiber with 0.55% HR6 finish. The total basis weight of the dual layer bonded carded composite was 75 gsm.

The aqueous formulation described in Example 1 was applied to the polyester/bicomponent fiber side of the dual layer bonded carded composite using a knife coater. A 0.75 osy spunbond/meltblown/spunbond (SMS) fabric was used as a carrier sheet to keep the aqueous formulation from contacting the components. The gap between the knife and steel roller that carried the bonded carded web and SMS fabrics was set at 1100 micrometers. The line speed was 0.25 meters per minute. The coater contained a four-foot drier set at 145° C. that was used to partially dry the coated fabric. The partially dried coated fabric was removed from the SMS carrier sheet and then cut into 17-inch pieces and placed in a laboratory oven at 110° C. for about 20 minutes to complete the drying step. When the coated fabric was removed from the SMS carrier sheet, it was observed that the aqueous formulation had not penetrated or wetted out the underside of the dual layer bonded carded web fabric. The concentration of the components of the exothermic composition was calculated from the coated and dried fabric pieces (41.8±2.0 grams), the untreated piece of fabric (5.0 grams), and the composition of the aqueous formulation. The results are set forth below in Table 4.

TABLE 4

Components of the Exothermic Composition

| Component | Calculated Amount |
|---|---|
| Iron | 76.1% |
| Activated Carbon | 4.6% |
| SM-100 | 2.2% |
| Elite PE | 4.3% |
| Sodium Chloride | 5.6% |
| Calcium Carbonate | 7.2% |
| Solids Add-On Level | ~728% |

EXAMPLE 5

The dual layer bonded carded composite of Example 4 was employed. The coating formulation was prepared as follows. In a 1-gallon metal pail, 70.7 grams of METOLOSE SM-100 (Shin-Etsu Chemical Co., Ltd.) and 159.9 grams of sodium chloride (Mallinckrodt) were added to 2511.5 grams of distilled water that was stirred and heated to 70° C. The mixture was stirred and allowed to partially cool for about 90 minutes. It was then further cooled with an ice bath while stirring from 34° C. to about 8° C. When the temperature of the aqueous SM-100 and salt solution had warmed to about 15° C., 1338.3 grams were transferred to another 1-gallon metal pail. While stirring, the following additional ingredients were then added sequentially: 129.0 grams of DUR-O-SET® Elite PE-LV 25432A ethylene-vinyl acetate emulsion (Celanese Emulsions), 278.8 grams of XP-5200 sample #06.3405204 calcium carbonate slurry (Omya), 72.0 grams of Nuchar SA-400 activated carbon (MeadWestvaco), and 1181.2 grams of A-131 iron powder (North American Höganäs). The viscosity of the aqueous coating formulation was measured at about 3500 centipoise using a Brookfield DV-1 viscometer with an LV-4 spindle set at 100 rpm. The calculated concentration of each component of the aqueous formulation is set forth below in Table 5.

TABLE 5

Components of the Aqueous Formulation

| Component | Calculated Amount |
|---|---|
| Iron | 39.4% |
| Activated Carbon | 2.4% |
| SM-100 | 1.2% |
| Elite PE-LV | 2.1% |
| Calcium Carbonate | 3.8% |
| Sodium Chloride | 2.6% |
| Water | 48.5% |

The aqueous formulation was applied to the polyester/bicomponent fiber side of the dual layer bonded carded composite using a knife coater. A 5"-wide roll of an airlaid fabric was used as a bottom layer to carry the coated bonded carded composite. The width of the coating was adjusted to 5 inches to match the width of the airlaid fabric. The airlaid fabric was formed from 75 wt. % wood pulp fluff (Weyerhaeuser NB416), 15 wt. % superabsorbent (Degussa SXM9543), and 10 wt. % of KoSa T255 bicomponent fiber, and had a basis weight of 225 grams per square meter and a density of 0.12 grams per cubic centimeter. The gap between the knife and steel roller that carried the bonded carded web and airlaid fabrics was set at 2250 micrometers. The line speed was 0.25 meters per minute. The coater contained a four-foot drier set at 120° C. that was used to partially dry the coated fabric. The partially dried coated fabric was attached to the bottom airlaid layer due to the aqueous formulation penetrating through the bonded carded web and contacting the airlaid. The partially dried coated laminate was cut into 17-inch pieces and placed in a laboratory oven at 120° C. for about 20 minutes to complete the drying step. The concentration of the components of the exothermic composition was calculated from the coated and dried laminate pieces (71.4±1.7 grams), the untreated pieces of bonded carded web and airlaid fabrics (13.8 grams), and the composition of the aqueous formulation. The results are set forth below in Table 6.

TABLE 6

Components of the Exothermic Composition

| Component | Calculated Amount |
|---|---|
| Iron | 76.6% |
| Activated Carbon | 4.7% |
| SM-100 | 2.2% |
| Elite PE | 4.1% |
| Sodium Chloride | 5.1% |
| Calcium Carbonate | 7.3% |
| Solids Add-On Level | ~417% |

Another batch of the aqueous coating formulation described above was prepared and produced the same components as shown in Table 5. The viscosity of this second batch of aqueous coating formulation was also measured at about 3500 centipoise using a Brookfield DV-1 viscometer with an LV-4 spindle set at 100 rpm. The aqueous formulation was applied to the polyester/bicomponent fiber side of the dual layer bonded carded composite in a process using a knife coater. A 0.75 osy spunbond/meltblown/spunbond (SMS) fabric was used as a carrier sheet to keep the aqueous formulation from contacting the components. The gap between the knife and steel roller that carried the bonded carded web and SMS fabrics was set at 900 micrometers. The line speed was 0.25 meters per minute. The coater contained a four-foot drier set at 145° C. that was used to partially dry the coated fabric. The partially dried coated fabric was removed from the SMS carrier sheet and then cut into 17-inch pieces and placed in a laboratory oven at 120° C. for about 20 minutes to complete the drying step. The concentration of the components of the exothermic composition was calculated from the coated and dried fabric pieces (57.1±0.8 grams), the untreated piece of fabric (4.5 grams), and the composition of the aqueous formulation. The results are set forth below in Table 7.

TABLE 7

Components of the Exothermic Composition

| Component | Calculated Amount |
|---|---|
| Iron | 76.5% |
| Activated Carbon | 4.7% |
| SM-100 | 2.2% |
| Elite PE-LV | 4.2% |
| Sodium Chloride | 5.1% |
| Calcium Carbonate | 7.3% |
| Solids Add-On Level | ~1169% |

A two-layered structure (3.25"×3.5") was then designed for activating the exothermic reaction. Specifically, the two-layered structure included one piece of the coated bonded carded web airlaid laminate and one piece of the coated bonded carded web. The uncoated side of the bonded carded composite was placed next to the airlaid side of the laminate. The airlaid side of the laminate was first wetted with 4.8 grams of an aqueous salt solution, an amount that increased the mass of the airlaid layer of the laminate by a factor of about 3.8. The salt solution contained 5.0 wt. % sodium chloride in distilled water. The weight of the coated laminate piece was 11.3 grams and the weight of the piece of coated bonded carded web was 5.9 grams. The total weight of iron for the two pieces combined was 12.4 grams. The two-layered structure was then placed inside of a rectangular pouch (4.25"×4.5") that was sealed with a heat sealer and reinforced with metallized tape. The pouch was made from a nylon spunbond microporous film laminate that had a layer of stapleknit fabric heat sealed to the nylon spunbond side. The laminate was obtained from Mitsubishi International Corp. and labeled TSF EDFH 5035-TYPE. The WVTR of the laminate was measured at 455 g/m$^2$/24 hrs by using the cup method (ASTM Standard E-96E-80). The stapleknit fabric was produced from 20% wood pulp fluff (50% Northern softwood kraft fibers/50% Alabama Pine bleached kraft softwood), 58% 1.5 denier polyester fiber (Invista Type 103), and 22% polypropylene spunbond (Kimberly-Clark Corp.). The resulting thermal device was heat sealed in a metallized storage bag for 1 day prior to activating the reaction. The metallized storage bag was KAL-ML5 from Kapak Corporation, a two-ply structure containing a metallized polyester layer that was adhesively laminated to a linear low density polyethylene film.

EXAMPLE 6

A thermal device was formed as described in Example 5. The weight of the coated bonded carded/airlaid laminate piece was 11.0 grams and the weight of the piece of coated bonded carded composite was 6.0 grams. The total weight of iron for the two pieces combined was 12.2 grams. The airlaid side of the laminate piece was wetted with 5.1 grams of an aqueous salt solution, an amount that increased the mass of the airlaid layer of the laminate by a factor of about 3.9. The salt solution contained 5.0 wt. % sodium chloride in distilled water. The resulting thermal device was heat sealed in a metallized storage bag for 1 day prior to activating the reaction.

EXAMPLE 7

A thermal device was formed as described in Example 5. The weight of the coated bonded carded/airlaid laminate piece was 11.5 grams and the weight of the piece of coated bonded carded composite was 6.0 grams. The total weight of iron for the two pieces combined was 12.6 grams. The airlaid side of the laminate piece was wetted with 5.0 grams of an aqueous salt solution, an amount that increased the mass of the airlaid layer of the laminate by a factor of about 3.8. The salt solution contained 5.0 wt. % sodium chloride in distilled water. The resulting thermal device was heat sealed in a metallized storage bag for 1 day prior to activating the reaction.

EXAMPLE 8

A thermal device was formed as described in Example 5. The weight of the coated bonded carded/airlaid laminate piece was 11.6 grams and the weight of the piece of coated bonded carded composite was 6.1 grams. The total weight of iron for the two pieces combined was 12.7 grams. The airlaid side of the laminate piece was wetted with 5.2 grams of an aqueous salt solution, an amount that increased the mass of the airlaid layer of the laminate by a factor of about 3.9. The salt solution contained 5.0 wt. % sodium chloride in distilled water. The resulting thermal device was heat sealed in a metallized storage bag for 1 day prior to activating the reaction.

EXAMPLE 9

Figure 3:
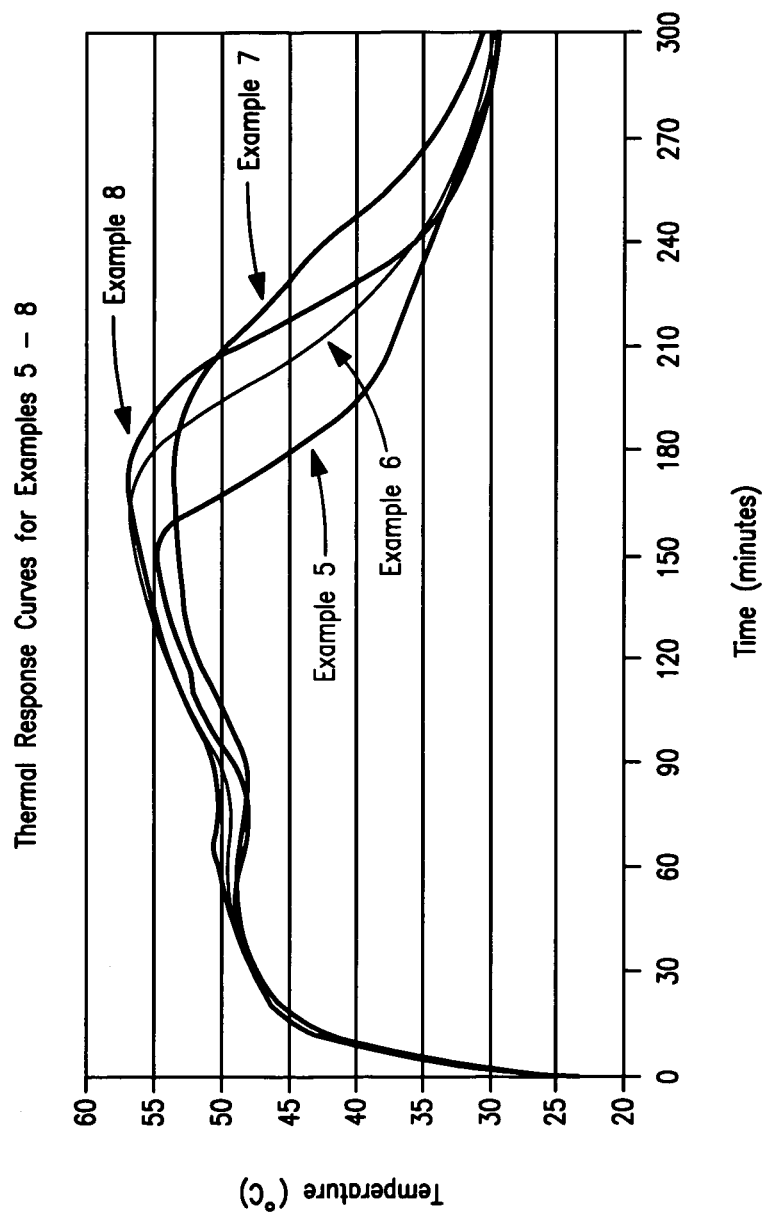
FIG. 3 is a thermal response curve showing temperature (° C.) versus time (minutes) for Examples 5-8.

The thermal devices of Examples 5, 6, 7, and 8 were tested by opening the metallized storage bags to initiate the reaction. Testing was conducted by attaching a thermocouple wired to a data collection device to one side of the thermal device. The temperature was recorded as a function of time (at 5 second intervals) to give the thermal response curves shown in FIG. 3. As illustrated, the thermal response curves for the devices of Examples 5, 6, 7, and 8 (all contained the exothermic moisture holding fabric laminate) reached 40° C. within about 10 minutes after opening the storage bag and then gradually increased in temperature as a function of time for at least another 2 hours. Among other things, this gradual increase in temperature (as a function of time) might help the user overcome thermal fatigue and thus continue to feel the warmth provided by the thermal device.

EXAMPLE 10

Initially, a 7"-wide roll of a dual layer bonded carded composite was provided. The first layer of the composite contained 100 gsm of a blend of 50% 15 denier (47.7 μm) Invista T-295 polyester fiber with 0.50% L1 finish and 50% of a 6.0 denier (30.7 μm) FiberVisions ESC 236 bicomponent (PE sheath/PP core) fiber with 0.55% HR6 finish. The second layer of the composite contained 17 gsm of a 100% 3.0 denier (25.8 μm) FiberVisions ESC 233 bicomponent (PE sheath/PP core) fiber with 0.55% HR6 finish. The total basis weight of the dual layer bonded carded web was 117 gsm.

The coating formulation was prepared as follows. In a 1-gallon metal pail, 84.5 grams of METOLOSE SM-100 (Shin-Etsu Chemical Co., Ltd.) and 191.1 grams of sodium chloride (Mallinckrodt) were added to 3000.0 grams of distilled water that was stirred and heated to 70° C. The mixture was stirred and allowed to partially cool for about 60 minutes. It was then further cooled with an ice bath while stirring from 41° C. to about 12° C. The following day, 2000.1 grams of the room temperature aqueous SM-100+sodium chloride solution were transferred to a 2-gallon metal pail. While stirring, the following additional ingredients were then added sequentially: 194.2 grams of DUR-O-SET® Elite PE-LV 25-432A ethylene-vinyl acetate emulsion (Celanese Emulsions), 416.9 grams of XP-5200 sample #06.3405204 calcium carbonate slurry (Omya), 107.6 grams of Nuchar SA-20 activated carbon (MeadWestvaco), and 1765.2 grams of A-131 iron powder (North American Höganäs). The viscosity of the aqueous coating formulation was measured at 3120 centipoise using a Brookfield DV-1 viscometer with an LV-4 spindle set at 100 rpm. The calculated concentration of each component of the aqueous formulation is set forth below in Table 8.

TABLE 8

Components of the Aqueous Formulation

| Component | Calculated Amount |
|---|---|
| Iron | 39.4% |
| Activated Carbon | 2.4% |
| SM-100 | 1.2% |
| Elite PE-LV | 2.1% |
| Calcium Carbonate | 3.8% |
| Sodium Chloride | 2.6% |
| Water | 48.5% |

The aqueous formulation was applied to the polyester/bicomponent fiber side of the dual layer bonded carded composite in a process using a knife coater. A 5"-wide roll of an airlaid fabric was used as a bottom layer to carry the coated bonded carded web fabric. The width of the coating was adjusted to 5 inches to match the width of the airlaid fabric. The airlaid fabric was formed from 73 wt. % wood pulp fluff (Weyerhaeuser NB416), 21 wt. % of Trevira T256 bicomponent fiber, and 6 wt. % Airflex 192 latex, and had a basis weight of 130 grams per square meter and a density of 0.08 grams per cubic centimeter. The gap between the knife and steel roller that carried the bonded carded web and airlaid fabrics was set at 2500 microns. The line speed was 0.25 meters per minute. The coater contained a four-foot drier set at 120° C. that was used to partially dry the coated fabric. The partially dried coated fabric was attached to the bottom airlaid layer due to the aqueous formulation penetrating through the bonded carded web and contacting the airlaid. The partially dried coated laminate was cut into 17-inch pieces and placed in a laboratory oven at 120° C. for about 20 minutes to complete the drying step. The concentration of the components of the exothermic composition was calculated from a 4.5-inch by 16-inch coated and dried laminate piece (109.3 grams), the untreated pieces of bonded carded web and airlaid fabrics (11.5 grams) of the same size, and the composition of the aqueous formulation. The results are set forth below in Table 9.

TABLE 9

Components of the Exothermic Composition

| Component | Calculated Amount |
|---|---|
| Iron | 76.6% |
| Activated Carbon | 4.7% |
| SM-100 | 2.2% |
| Elite PE | 4.2% |
| Sodium Chloride | 5.0% |
| Calcium Carbonate | 7.3% |
| Solids Add-On Level | ~850% |

A one-layered structure (3.25"×3.5") was then designed for activating the exothermic reaction. Specifically, the one-layered structure was one piece of the coated bonded carded/airlaid laminate. The airlaid side of the laminate was first wetted with 3.9 grams of an aqueous salt solution, an amount that increased the mass of the airlaid layer of the laminate by a factor of about 3.9. The salt solution contained 10.0 wt. % sodium chloride in distilled water. The weight of the coated laminate piece was 17.2 grams (11.8 grams iron). The one-layered structure was then placed inside of a rectangular pouch (4.25"×4.5") that was sealed with a heat sealer and reinforced with metallized tape. The pouch was made from a nylon spunbond microporous film laminate that had a layer of stapleknit fabric heat sealed to the nylon spunbond side. The laminate was obtained from Mitsubishi International Corp. and labeled TSF EDFH 5035-TYPE. The WVTR of the laminate was measured at 455 g/m$^2$/24 hrs by using the cup method (ASTM Standard E-96E-80). The stapleknit fabric was produced from 20% wood pulp fluff (50% Northern softwood kraft fibers/50% Alabama Pine bleached kraft softwood), 58% 1.5 denier polyester fiber (Invista Type 103), and 22% polypropylene spunbond (Kimberly-Clark Corp.). The resulting thermal device was heat sealed in a metallized storage bag for 21.5 hours prior to activating the reaction. The metallized storage bag was KAL-ML5 from Kapak Corporation, a two-ply structure containing a metallized polyester layer that was adhesively laminated to a linear low density polyethylene film.

EXAMPLE 11

A thermal device was formed as described in Example 10. The weight of the coated bonded carded/airlaid laminate piece was 16.9 grams (11.5 grams of iron). The airlaid side of the laminate piece was wetted with 3.9 grams of an aqueous salt solution, an amount that increased the mass of the airlaid layer of the laminate by a factor of about 3.9. The salt solution contained 10 wt. % sodium chloride in distilled water. The resulting thermal device was heat sealed in a metallized storage bag for 21.5 hours prior to activating the reaction.

EXAMPLE 12

Figure 4:
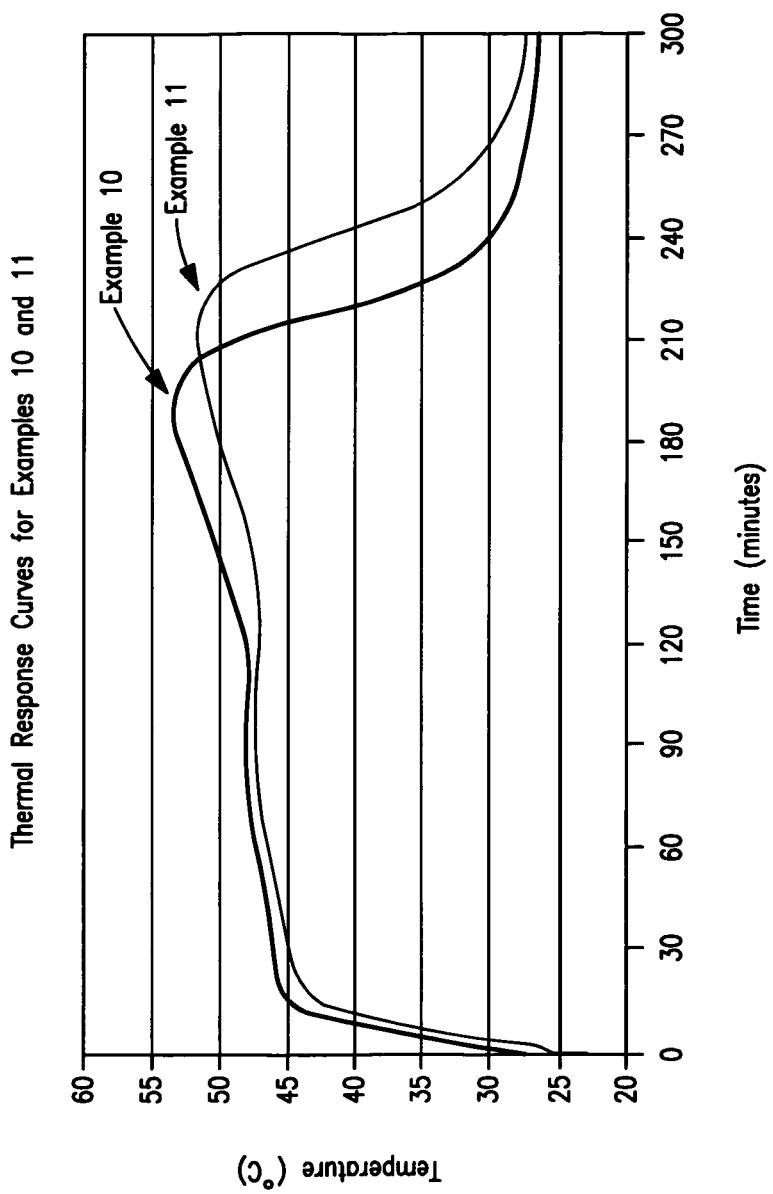
FIG. 4 is a thermal response curve showing temperature (° C.) versus time (minutes) for Examples 10 and 11.

The thermal devices of Examples 10 and 11 were tested. The metallized storage bags for the devices of these Examples were opened to initiate the reaction. Testing was conducted by attaching a thermocouple wired to a data collection device to one side of the thermal device. The temperature was recorded as a function of time (at 5 second intervals) to give the thermal response curves shown in FIG. 4. As illustrated, the thermal response curves for the devices of Examples 10 and 11 (each contained only one layer of an exothermic moisture holding fabric laminate) reached 40° C. within about 10 minutes after opening the storage bag and then gradually increased in temperature as a function of time for at least another 3 hours. This gradual increase in temperature as a function of time is thought to help the user overcome thermal fatigue and thus continue to feel the warmth provided by the thermal device.

EXAMPLE 13

The coated bonded carded/airlaid laminate described in Example 10 was used. A two-layered structure (4"×9.5") was then designed for activating the exothermic reaction. Specifically, the two-layered structure included two pieces of the coated bonded carded web airlaid laminate positioned with the airlaid side of each piece facing each other. The airlaid side of each piece of the laminate was first wetted with 10.1 and 10.8 grams of an aqueous salt solution, an amount that increased the mass of the airlaid layer of the laminate by a factor of about 3.1. The salt-solution contained 10.0 wt. % sodium chloride in distilled water. The total weight of the two coated laminate pieces was 111.1 grams (85.0 grams of iron). The two-layered structure was then placed inside of a rectangular pouch (5"×10.5") that was sealed with a heat sealer. The pouch was made from a nylon spunbond microporous film laminate. The laminate was obtained from Mitsubishi International Corp. and labeled TSF EDFH 5035-TYPE. The WVTR of the laminate was measured at 455 g/m²/24 hrs by using the cup method (ASTM Standard E-96E-80). The resulting thermal device was heat sealed in a metallized storage bag for 13 days prior to activating the reaction. The metallized storage bag was KAL-ML5 from Kapak Corporation, a two-ply structure containing a metallized polyester layer that was adhesively laminated to a linear low density polyethylene film.

EXAMPLE 14

Figure 5:
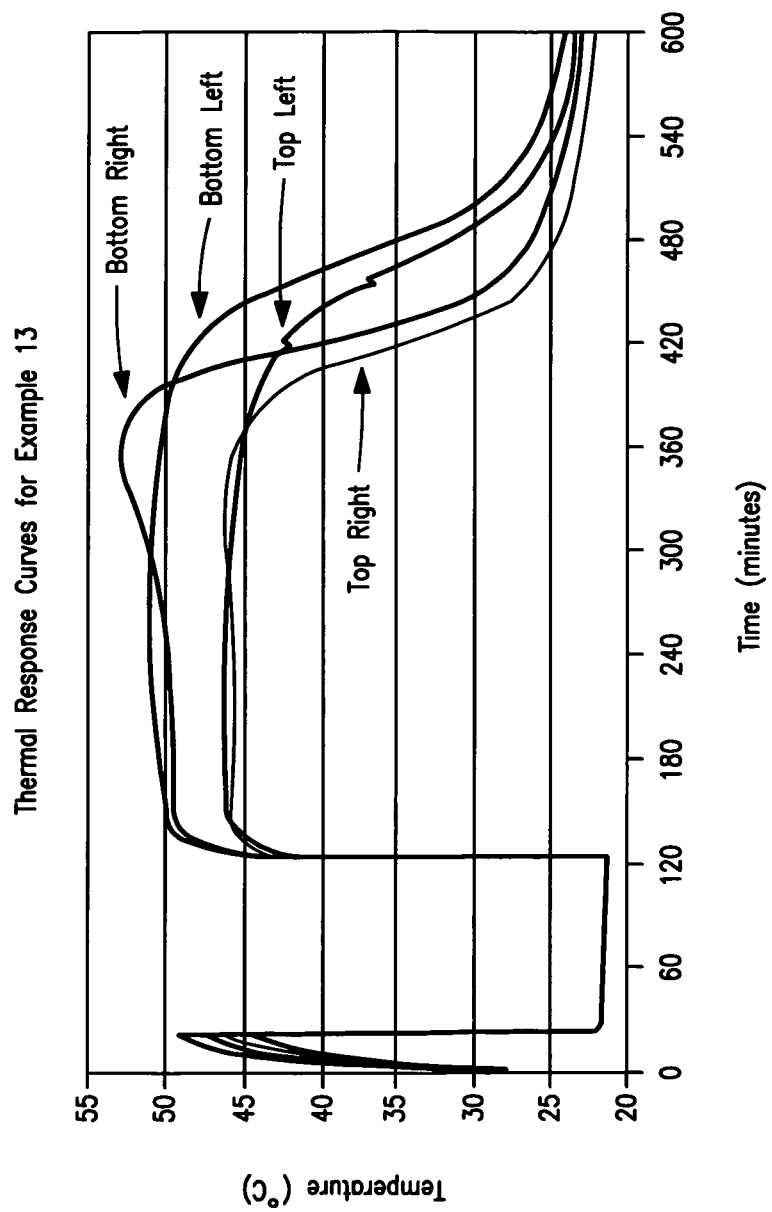
FIG. 5 is a thermal response curve showing temperature (° C.) versus time (minutes) for Example 13.

The thermal device of Example 13 was tested. The metallized storage bag for the device of Example 13 was opened to initiate the reaction. Testing was conducted by attaching four thermocouples wired to a data collection device to the thermal device. Two thermocouples were attached to the bottom side of the device and two thermocouples were attached to the top side of the device. The bottom side of the device was in contact with bubble wrap while the top side was in contact with air. The temperature of each thermocouple was recorded as a function of time (at 5 second intervals) to give the thermal response curves shown in FIG. 5. As illustrated, the thermal response curves for the device of Example 13 reached 40° C. within about 10 minutes after opening the storage bag. At 30 minutes the device was removed from the thermocouples for evaluations. The device was again attached to the thermocouples at about 120 minutes from the time it was removed from the metallized storage bags. As illustrated in FIG. 5, the device continued to provide warmth that lasted for a total time of least 7 hours. The temperature of each side was also uniform in heat output, producing constant temperatures of about 50° C. for the bottom side and about 45° C. for the top side.

EXAMPLE 15

Initially, a 7"-wide roll of a single layer bonded carded web was provided. The web contained a blend of 40% 6.0 denier (31.1 µm) Invista T-295 polyester fiber with 0.50% L1 finish and 60% of a 3.0 denier (25.9 µm) FiberVisions ESC 233 bicomponent (PE sheath/PP core) fiber with 0.55% HR6 finish, and had a basis weight of 85 gsm. The aqueous formulation described in Example 10 was applied to the bonded carded web in a process using a knife coater. A 5"-wide roll of an airlaid fabric was used as a bottom layer to carry the coated bonded carded web. The width of the coating was adjusted to 5 inches to match the width of the airlaid fabric. The airlaid fabric was formed from 73 wt. % wood pulp fluff (Weyerhaeuser NB416), 21 wt. % of Trevira T256 bicomponent fiber, and 6 wt. % Airflex 192 latex, and had a basis weight of 130 grams per square meter and a density of 0.08 grams per cubic centimeter. The gap between the knife and steel roller that carried the bonded carded web and airlaid fabrics was initially set at 1800 micrometers. The line speed was 0.25 meters per minute. The coater contained a four-foot drier set at 120° C. that was used to partially dry the coated fabric. When the coated bonded carded web fabric and bottom airlaid layer were removed from the oven, it was observed that the aqueous formulation had not penetrated or wetted out the underside of the bonded carded web fabric and had therefore not attached it to the airlaid fabric. The gap between the knife and steel roller that carried the bonded carded web and airlaid fabrics was then set at 2600 micrometers, but the coated bonded carded web was still not attached to the airlaid fabric.

EXAMPLE 16

Initially, a 7"-wide roll of a dual layer bonded carded composite of Example 16 was provided. The first layer of the composite contained 50 gsm of a blend of 50% 15 denier (44.8 µm) Invista T-295 polyester fiber with 0.50% L1 finish and 50% of a 15 denier (59.1 µm) FiberVisions ESC bicomponent (PE sheath/PP core) fiber with 0.55% HR6 finish. The second layer of the composite contained 17 gsm of a 100% 3.0 denier (24.3 µm) FiberVisions ESC 233 bicomponent (PE sheath/PP core) fiber with 0.55% HR6 finish. The total basis weight of the dual layer bonded carded web was 67 gsm.

The aqueous formulation described in Example 10 was applied to the polyester/bicomponent fiber side of the dual layer bonded carded composite in a process using a knife coater. A 5"-wide roll of an airlaid fabric was used as a bottom layer to carry the coated bonded carded web fabric. The width of the coating was adjusted to 5 inches to match the width of the airlaid fabric. The airlaid fabric was formed from 73 wt. % wood pulp fluff (Weyerhaeuser NB416), 21 wt. % of Trevira T256 bicomponent fiber, and 6 wt. % Airflex 192 latex, and had a basis weight of 130 grams per square meter and a density of 0.08 grams per cubic centimeter. The gap between the knife and steel roller that carried the bonded carded web and airlaid fabrics was set at 2000 micrometers. The line speed was 0.45 meters per minute. The coater contained a four-foot drier set at 120° C. that was used to partially dry the coated fabric. The partially dried coated fabric was attached to the bottom airlaid layer due to the aqueous formulation penetrating through the bonded carded composite and contacting the airlaid. The partially dried coated laminate was cut into 17-inch pieces and placed in a laboratory oven at 120° C. for about 20 minutes to complete the drying step. The concentration of the components of the exothermic composition was calculated from the coated and dried laminate pieces (73.3±2.1 grams), the untreated pieces of bonded carded web and airlaid fabric (11.4 grams) of the same size, and the composition of the aqueous formulation. The results are set forth below in Table 10.

TABLE 10

Components of the Exothermic Composition

| Component | Calculated Amount |
|---|---|
| Iron | 76.6% |
| Activated Carbon | 4.7% |
| SM-100 | 2.2% |
| Elite PE | 4.2% |
| Sodium Chloride | 5.0% |
| Calcium Carbonate | 7.3% |
| Solids Add-On Level | ~543% |

EXAMPLE 17

The dual layer bonded carded composite of Example 16 was provided. A coating formulation was prepared as follows. In a 1-gallon metal pail, 84.5 grams of METOLOSE SM-100 (Shin-Etsu Chemical Co., Ltd.) and 191.1 grams of sodium chloride (Mallinckrodt) were added to 3000.0 grams of distilled water that was stirred and heated to 70° C. The mixture was stirred and allowed to partially cool for about 60 minutes. It was then further cooled with an ice bath while stirring from 41° C. to about 12° C. The following day, 1337.9 grams of the room temperature aqueous SM-100+sodium chloride solution were transferred to a 2-gallon metal pail. While stirring, the following additional ingredients were then added sequentially: 131.0 grams of DUR-O-SET® Elite PE-LV 25-432A ethylene-vinyl acetate emulsion (Celanese Emulsions), 279.3 grams of XP-5200 sample #06.3405204 calcium carbonate slurry (Omya), 72.0 grams of Nuchar SA-20 activated carbon (MeadWestvaco), and 1181.0 grams of NF-325 iron powder (North American Höganäs). The viscosity of the aqueous coating formulation was measured at 2148 centipoise using a Brookfield DV-1 viscometer with an LV-4 spindle set at 100 rpm. The calculated concentration of each component of the aqueous formulation is set forth below in Table 11.

TABLE 11

Components of the Aqueous Formulation

| Component | Calculated Amount |
|---|---|
| Iron | 39.4% |
| Activated Carbon | 2.4% |
| SM-100 | 1.2% |
| Elite PE-LV | 2.2% |
| Calcium Carbonate | 3.8% |
| Sodium Chloride | 2.6% |
| Water | 48.4% |

The aqueous formulation was applied to the polyester/bicomponent fiber side of the dual layer bonded carded composite in a process using a knife coater. A 5"-wide roll of an airlaid fabric was used as a bottom layer to carry the coated bonded carded web fabric. The width of the coating was adjusted to 5 inches to match the width of the airlaid fabric. The airlaid fabric was formed from 73 wt. % wood pulp fluff (Weyerhaeuser NB416), 21 wt. % of Trevira T256 bicomponent fiber, and 6 wt. % Airflex 192 latex, and had a basis weight of 130 grams per square meter and a density of 0.08 grams per cubic centimeter. The gap between the knife and steel roller that carried the bonded carded web and airlaid fabrics was set at 2000 micrometers. The line speed was 0.45 meters per minute. The coater contained a four-foot drier set at 120° C. that was used to partially dry the coated fabric. The partially dried coated fabric was attached to the bottom airlaid layer due to the aqueous formulation penetrating through the bonded carded web and contacting the airlaid. The partially dried coated laminate was cut into 17-inch pieces and placed in a laboratory oven at 120° C. for about 20 minutes to complete the drying step. The concentration of the components of the exothermic composition was calculated from coated and dried laminate pieces (78.5±1.7 grams), the untreated pieces of bonded carded composite and airlaid fabric (11.4 grams) of the same size, and the composition of the aqueous formulation. The results are set forth below in Table 12.

TABLE 12

Components of the Exothermic Composition

| Component | Calculated Amount |
|---|---|
| Iron | 76.5% |
| Activated Carbon | 4.7% |
| SM-100 | 2.2% |
| Elite PE | 4.2% |
| Sodium Chloride | 5.1% |
| Calcium Carbonate | 7.3% |
| Solids Add-On Level | ~589% |

EXAMPLE 18

The dual layer bonded carded composite of Example 16 was provided. A coating formulation was prepared as follows. In a 1-gallon metal pail, 84.5 grams of METOLOSE SM-100 (Shin-Etsu Chemical Co., Ltd.) and 191.0 grams of sodium chloride (Mallinckrodt) were added to 3000.0 grams of distilled water that was stirred and heated to 70° C. The mixture was stirred and allowed to partially cool for about 60 minutes. It was then further cooled with an ice bath while stirring from 41° C. to about 12° C. The following day, 1338.3 grams of the room temperature aqueous SM-100+sodium chloride solution were transferred to a 2-gallon metal pail. While stirring, the following additional ingredients were then added sequentially: 130.4 grams of DUR-O-SET® Elite PE-LV 25-432A ethylene-vinyl acetate emulsion (Celanese Emulsions), 280.2 grams of XP-5200 sample #06.3405204 calcium carbonate slurry (Omya), 72.0 grams of Nuchar SA-20 activated carbon (MeadWestvaco), and 1181.0 grams of NFX-325 iron powder (North American Höganäs). The viscosity of the aqueous coating formulation was measured at about 2700 centipoise using a Brookfield DV-1 viscometer with an LV-4 spindle set at 100 rpm. The calculated concentration of each component of the aqueous formulation is set forth below in Table 13.

TABLE 13

Components of the Aqueous Formulation

| Component | Calculated Amount |
|---|---|
| Iron | 39.3% |
| Activated Carbon | 2.4% |
| SM-100 | 1.2% |
| Elite PE-LV | 2.2% |
| Calcium Carbonate | 3.8% |
| Sodium Chloride | 2.6% |
| Water | 48.5% |

The aqueous formulation was applied to the polyester/bicomponent fiber side of the dual layer bonded carded composite in a process using a knife coater. A 5"-wide roll of an airlaid fabric was used as a bottom layer to carry the coated bonded carded web fabric. The width of the coating was adjusted to 5 inches to match the width of the airlaid fabric.

The airlaid fabric was formed from 73 wt. % wood pulp fluff (Weyerhaeuser NB416), 21 wt. % of Trevira T256 bicomponent fiber, and 6 wt. % Airflex 192 latex, and had a basis weight of 130 grams per square meter and a density of 0.08 grams per cubic centimeter. The gap between the knife and steel roller that carried the bonded carded web and airlaid fabrics was set at 2000 micrometers. The line speed was 0.45 meters per minute. The coater contained a four-foot drier set at 120° C. that was used to partially dry the coated fabric. The partially dried coated fabric was attached to the bottom airlaid layer due to the aqueous formulation penetrating through the bonded carded web and contacting the airlaid. The partially dried coated laminate was cut into 17-inch pieces and placed in a laboratory oven at 120° C. for about 20 minutes to complete the drying step. The concentration of the components of the exothermic composition was calculated from coated and dried laminate pieces (79.0±0.9 grams), the untreated pieces of bonded carded composite and airlaid fabric (11.4 grams) of the same size, and the composition of the aqueous formulation. The results are set forth below in Table 14.

TABLE 14

Components of the Exothermic Composition

| Component | Calculated Amount |
|---|---|
| Iron | 76.5% |
| Activated Carbon | 4.7% |
| SM-100 | 2.2% |
| Elite PE | 4.2% |
| Sodium Chloride | 5.0% |
| Calcium Carbonate | 7.4% |
| Solids Add-On Level | ~593% |

EXAMPLE 19

Initially, a 7"-wide roll of a dual layer bonded carded composite was provided. The first layer of the composite contained 17 gsm of a 100% 1.5 denier (20.9 μm) FiberVisions ESC 215 bicomponent (PE sheath/PP core) fiber with 0.55% HR6 finish. The second layer of the composite contained 50 gsm of a blend of 50% 6.0 denier (27.6 μm) Invista T-295 polyester fiber with 0.50% L1 finish and 50% of a 6.0 denier (34.3 μm) FiberVisions ESC 236 bicomponent (PE sheath/PP core) fiber with 0.55% HR6 finish. The total basis weight of the dual layer bonded carded web was 67 gsm.

The aqueous formulation described in Example 18 was applied to the polyester/bicomponent fiber side of the dual layer bonded carded composite in a process using a knife coater. A 5"-wide roll of an airlaid fabric was used as a bottom layer to carry the coated bonded carded composite. The width of the coating was adjusted to 5 inches to match the width of the airlaid fabric. The airlaid fabric was formed from 73 wt. % wood pulp fluff (Weyerhaeuser NB416), 21 wt. % of Trevira T256 bicomponent fiber, and 6 wt. % Airflex 192 latex, and had a basis weight of 130 grams per square meter and a density of 0.08 grams per cubic centimeter. The gap between the knife and steel roller that carried the bonded carded web and airlaid fabrics was set at 2000 micrometers. The line speed was 0.45 meters per minute. The coater contained a four-foot drier set at 120° C. that was used to partially dry the coated fabric. The partially dried coated fabric appeared to be attached to the bottom airlaid layer due to the aqueous formulation penetrating through the bonded carded web and contacting the airlaid. However, after the partially dried coated material was cut into 17-inch pieces and placed in a laboratory oven at 120° C. for about 20 minutes to complete the drying step, it was observed that the coated bonded carded web was only weakly attached to the airlaid fabric.

EXAMPLE 20

Various properties of the aforementioned bonded carded web samples were determined, including basis weight, caliper (or bulk thickness), density, and permeability. The results are set forth below in Table 15.

TABLE 15

Web Properties

| Examples | Web Type | Layers | Kozeny-Carman Permeability (Darcies) | Ratio of Kozeny-Carman Perm. ($1^{st}/2^{nd}$) | du Plessis Permeability (Darcies) | Ratio of du Plessis Perm. ($1^{st}/2^{nd}$) | Basis Weight (gsm) | Bulk (mm) | Density (g/cm³) |
|---|---|---|---|---|---|---|---|---|---|
| 1-2 | Single layer bonded carded fabric | — | 1,758 | — | 2,645 | — | 53 | 1.45 | 0.037 |
| 4-9 | Dual layer bonded carded fabric | $1^{st}$ $2^{nd}$ | 3,295 559 | 5.9 | 4,391 706 | 6.2 | 62 | 1.18 | 0.052 |
| 10-14 | Dual layer bonded carded fabric | $1^{st}$ $2^{nd}$ | 6,842 2,707 | 2.5 | 11,845 4,426 | 2.8 | 108 | 4.24 | 0.025 |
| 15 | Single layer bonded carded fabric | — | 1,998 | — | 2,979 | — | 85 | 2.26 | 0.038 |
| 16-18 | Dual layer bonded carded fabric | $1^{st}$ $2^{nd}$ | 15,506 2,402 | 6.5 | 26,842 3,927 | 6.8 | 73 | 2.67 | 0.027 |

TABLE 15-continued

Web Properties

| Examples | Web Type | Layers | Kozeny-Carman Permeability (Darcies) | Ratio of Kozeny-Carman Perm. ($1^{st}/2^{nd}$) | du Plessis Permeability (Darcies) | Ratio of du Plessis Perm. ($1^{st}/2^{nd}$) | Basis Weight (gsm) | Bulk (mm) | Density (g/cm³) |
|---|---|---|---|---|---|---|---|---|---|
| 19 | Dual layer bonded carded fabric | $1^{st}$ $2^{nd}$ | 5,903 2,014 | 2.5 | 10,486 3,382 | 2.7 | 63 | 2.74 | 0.023 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A warming product comprising:
a thermal composite that includes a first fibrous layer positioned adjacent to and in contact with a second fibrous layer, a permeability of the first fibrous layer being greater than a permeability of the second fibrous layer, the warming product product further comprising an exothermic composition distributed through the first fibrous layer and the second fibrous layer of the composite, the exothermic composition comprising a metal configured to undergo an exothermic reaction upon exposure to oxygen and moisture, the exothermic composition further comprising a carbon component and metal halide;
a moisture-holding layer positioned adjacent to the second fibrous layer and adjacent an exterior of the thermal composite of the thermal composite, the moisture-holding layer containing an absorbent web that includes cellulosic fibers, wherein at least a portion of the exothermic composition is in contact with the moisture-holding layer and adheres the thermal composite thereto; and
an aqueous solution contained within the moisture-holding layer that is capable of supplying moisture to the exothermic composition.

2. The warming product of claim 1, wherein the ratio of the permeability of the first fibrous layer to the permeability of the second fibrous layer is about 1.5 or more.

3. The warming product of claim 1, wherein the ratio of the permeability of the first fibrous layer to the permeability of the second fibrous layer is from about 2.5 to about 8.0.

4. The warming product of claim 1, wherein the Kozeny-Carman permeability of the first layer is from about 1,500 to about 20,000 Darcies and the Kozeny-Carman permeability of the second fibrous layer is from about 300 to about 4000 Darcies.

5. The warming product of claim 1, wherein the du Plessis permeability of the first layer is from about 2,500 to about 35,000 Darcies and the du Plessis permeability of the second fibrous layer is from about 500 to about 6000 Darcies.

6. The warming product of claim 1, wherein the basis weight of the second fibrous layer is less than the basis weight of the first fibrous layer.

7. The warming product of claim 6, wherein the second fibrous layer has a basis weight of from about 1 to about 100 grams per square meter, and the first fibrous layer has a basis weight of from about 25 to about 500 grams per square meter.

8. The warming product of claim 1, wherein the caliper of the second fibrous layer is less than the caliper of the first fibrous layer.

9. The warming product of claim 8, wherein the second fibrous layer has a caliper of from about 0.1 to about 0.5 millimeter, and the first fibrous layer has a caliper of from about 1.5 to about 4 millimeters.

10. The warming product of claim 1, wherein the first fibrous layer comprises first synthetic fibers and the second fibrous layer comprises second synthetic fibers, wherein the average denier of the first synthetic fibers is greater than the average denier of the second synthetic fibers.

11. The warming product of claim 10, wherein the ratio of the average denier of the first synthetic fibers to the average denier of the second synthetic fibers is about 1.5 or more.

12. The warming product of claim 10, wherein the ratio of the average denier of the first synthetic fibers to the average denier of the second synthetic fibers is from about 2.0 to about 10.0.

13. The warming product of claim 10, wherein the average denier of the first synthetic fibers is from about 3 to about 30.

14. The warming product of claim 10, wherein the average denier of the second synthetic fibers is from about 0.1 to about 10.

15. The warming product of claim 10, wherein the first synthetic fibers include a mixture of small denier fibers and large denier fibers.

16. The warming product of claim 15, wherein the small denier fibers have a denier of from about 2 to about 10 and the large denier fibers have a denier of from about 4 to about 20.

17. The warming product of claim 1, wherein the first fibrous layer, the second fibrous layer, or both, contain a nonwoven web.

18. The warming product of claim 17, wherein the nonwoven web is a bonded carded web.

19. The warming product of claim 1, wherein the first fibrous layer, the second fibrous layer, or both, contain a treatment composition for enhancing wettability.

20. The warming product of claim 1, wherein the aqueous solution comprises one or more solutes.

21. The warming product of claim 1, wherein the solutes constitute from about 1 to about 20 wt.% of the aqueous solution.

22. The warming product of claim 1, wherein the vapor pressure of the aqueous solution is less than about 27.2 mm Hg at 25° C.

23. The warming product of claim 1, wherein the aqueous solution is present in an amount of from about 20 wt.% to about 500 wt.% of the weight of the metal.

24. The warming product of claim 1, wherein the moisture-holding layer contains a fibrous web having a basis weight of from about 50 to about 500 grams per square meter and a density of from about 0.05 to about 0.25 grams per cubic centimeters.

25. The warming product of claim 1, wherein the moisture-holding layer contains cellulosic fibers.

26. The warming product of claim 1, wherein the metal is iron, zinc, aluminum, magnesium, or combinations thereof.

27. The warming product of claim 1, wherein the exothermic composition further comprises a binder.

28. A method for forming a warming product that contains a thermal composite, the thermal composite including a first fibrous layer positioned adjacent to and in contact with a second fibrous layer, wherein the method comprises:

forming an exothermic coating formulation that comprises a metal configured to undergo an exothermic reaction upon exposure to oxygen and moisture, the exothermic formulation further comprising a carbon component and metal halide;

positioning a moisture-holding layer adjacent to the second fibrous layer and adjacent an exterior of the thermal composite of the thermal composite, wherein the moisture-holding layer contains an absorbent web that includes cellulosic fibers;

applying an aqueous solution to the moisture-holding layer; and applying the exothermic coating formulation to one or more surfaces of the thermal composite so that at least a portion of the formulation flows through the first fibrous layer and the second fibrous layer and contacts the moisture-holding layer, the formulation adhering the moisture-holding layer to the thermal composite.

29. The method of claim 28, wherein the first fibrous layer, the second fibrous layer, or both, contain a nonwoven web.

30. The method of claim 29, wherein the nonwoven web is a bonded carded web.

31. The method of claim 28, wherein the aqueous solution contains one or more solutes.

32. The method of claim 28, wherein the metal is iron, zinc, aluminum, magnesium, or combinations thereof.

33. The method of claim 28, wherein the exothermic coating formulation comprises a solvent.

34. The method of claim 28, wherein the exothermic coating formulation comprises a binder.

35. The method of claim 28, further comprising drying the thermal composite.

36. The warming product of claim 1, wherein said carbon component is activated carbon.

* * * * *

UNITED STATES PATENT AND TRADEMARK OFFICE
CERTIFICATE OF CORRECTION

PATENT NO. : 8,425,578 B2  
APPLICATION NO. : 11/513830  
DATED : April 23, 2013  
INVENTOR(S) : Roger B. Quincy, III et al.

Page 1 of 1

It is certified that error appears in the above-identified patent and that said Letters Patent is hereby corrected as shown below:

In the Claims:

In Claim 1 (column 39, ll. 37-38):

"...and adjacent an exterior of the thermal composite of the thermal composite..." should read
--...and adjacent an exterior of the thermal composite...--

In Claim 28 (column 41, ll. 19-20):

"...and adjacent an exterior of the thermal composite of the thermal composite..." should read
--...and adjacent an exterior of the thermal composite...--

Signed and Sealed this
Sixth Day of August, 2013

Teresa Stanek Rea
*Acting Director of the United States Patent and Trademark Office*